(12) United States Patent
Pemberton et al.

(10) Patent No.: US 9,994,631 B2
(45) Date of Patent: Jun. 12, 2018

(54) SIGNAL BIOMARKERS

(71) Applicant: OTAGO INNOVATION LIMITED, Dunedin (NZ)

(72) Inventors: Christopher Joseph Pemberton, Christchurch (NZ); Arthur Mark Richards, Christchurch (NZ)

(73) Assignee: UPSTREAM MEDICAL TECHNOLOGIES LIMITED, Christchurch Central (NZ)

( * ) Notice: Subject to any disclaimer, the term of this patent is extended or adjusted under 35 U.S.C. 154(b) by 0 days. days.

(21) Appl. No.: 14/691,562

(22) Filed: Apr. 20, 2015

(65) Prior Publication Data

US 2015/0353632 A1 Dec. 10, 2015

Related U.S. Application Data

(62) Division of application No. 13/186,447, filed on Jul. 19, 2011, now Pat. No. 9,103,840.

(60) Provisional application No. 61/365,677, filed on Jul. 19, 2010.

(51) Int. Cl.
| | | |
|---|---|---|
| *C07K 16/18* | (2006.01) | |
| *C07K 7/06* | (2006.01) | |
| *C07K 7/08* | (2006.01) | |
| *G01N 33/74* | (2006.01) | |
| *C07K 16/22* | (2006.01) | |
| *C07K 16/26* | (2006.01) | |

(52) U.S. Cl.
CPC .............. *C07K 16/18* (2013.01); *C07K 7/06* (2013.01); *C07K 7/08* (2013.01); *C07K 16/22* (2013.01); *C07K 16/26* (2013.01); *G01N 33/74* (2013.01); *G01N 33/746* (2013.01); *C07K 2317/24* (2013.01); *C07K 2317/34* (2013.01); *C07K 2317/76* (2013.01); *G01N 2333/505* (2013.01); *G01N 2333/58* (2013.01); *G01N 2800/324* (2013.01); *G01N 2800/325* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,816,567 A | 3/1989 | Cabilly et al. | |
| 5,221,685 A | 6/1993 | Obata et al. | |
| 5,310,687 A | 5/1994 | Bard et al. | |
| 5,334,708 A | 8/1994 | Chang et al. | |
| 5,480,792 A | 1/1996 | Buechler et al. | |
| 5,504,013 A | 4/1996 | Senior | |
| 5,525,524 A | 6/1996 | Buechler et al. | |
| 5,571,698 A | 11/1996 | Ladner et al. | |
| 5,631,171 A | 5/1997 | Sandstrom et al. | |
| 5,647,124 A | 7/1997 | Chan et al. | |
| 5,679,526 A | 10/1997 | Buechler et al. | |
| 5,719,060 A | 2/1998 | Hutchens et al. | |
| 5,719,600 A | 2/1998 | Alcorn | |
| 5,744,305 A | 4/1998 | Fodor et al. | |
| 5,792,294 A | 8/1998 | Randazzo et al. | |
| 5,821,047 A | 10/1998 | Garrard et al. | |
| 5,824,799 A | 10/1998 | Buechler et al. | |
| 5,843,708 A | 12/1998 | Hardman et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,947,124 A | 9/1999 | Buechler et al. | |
| 5,955,377 A | 9/1999 | Maul et al. | |
| 5,985,579 A | 11/1999 | Buechler et al. | |
| 6,019,944 A | 2/2000 | Buechler | |
| 6,020,153 A | 2/2000 | Hardman et al. | |
| 6,057,098 A | 5/2000 | Buechler et al. | |
| 6,107,623 A | 8/2000 | Bateman et al. | |
| 6,113,855 A | 9/2000 | Buechler | |
| 6,124,137 A | 9/2000 | Hutchens et al. | |
| 6,143,576 A | 11/2000 | Buechler | |
| 6,204,500 B1 | 3/2001 | Whitehouse et al. | |
| 6,225,047 B1 | 5/2001 | Hutchens et al. | |
| 6,235,241 B1 | 5/2001 | Catt et al. | |
| 6,268,144 B1 | 7/2001 | Koster | |
| 6,329,209 B1 | 12/2001 | Wagner et al. | |
| 6,399,398 B1 | 6/2002 | Cunningham et al. | |
| 6,780,645 B2 | 8/2004 | Hayter et al. | |
| 7,045,366 B2 | 5/2006 | Huang et al. | |
| 7,057,165 B2 | 6/2006 | Koopman et al. | |
| 7,476,724 B2 | 1/2009 | Dennis et al. | |
| 8,298,772 B2 | 10/2012 | Pemberton et al. | |
| 8,507,209 B2 | 8/2013 | Pemberton et al. | |

(Continued)

FOREIGN PATENT DOCUMENTS

| | | |
|---|---|---|
| WO | 2005/003154 A2 | 1/2005 |
| WO | 2005/052593 A1 | 6/2005 |

(Continued)

OTHER PUBLICATIONS

Hama et al. (J Endocrinology, Jun. 1994; 141 (3) 473-9, Abstract Only).*
Scopes (Ed.), Protein Purification: Principles and Practice, 1987, Springer-Verlag, NY (Table of Contents).
Scott et al., Searching for Peptide Ligands with an Epitope Library, Science, 1990, 386-390, 249(4967).
Sharma et al., Radiological imaging in pneumonia: recent innovations, Curr. Opin. Pulm. Med., 2007, 159-169, 13(3).
Skowera et al., CTLs are targeted to kill beta cells in patients with type 1 diabetes through recognition of a glucose-regulated preproinsulin epitope, J. Clin. Invest., 2008, 3390-3402, 118(10).
Skyler, Non-insulin-dependent diabetes mellitus: a clinical strategy, Diabetes Care, 1984, 118-129, Suppl. 1.

(Continued)

*Primary Examiner* — Lisa V Cook
(74) *Attorney, Agent, or Firm* — Carol L. Francis; Bozicevic, Field & Francis LLP

(57) ABSTRACT

Diagnostics relating to C-type natriuretic and erythropoietin signal peptides and fragments, and kits, uses and applications therefore.

17 Claims, 6 Drawing Sheets

(56) References Cited

U.S. PATENT DOCUMENTS

| | | | |
|---|---|---|---|
| 9,103,840 B2 * | 8/2015 | Pemberton | G01N 33/74 |
| 2003/0054494 A1 | 3/2003 | Desauvage et al. | |
| 2003/0083251 A1 | 5/2003 | Westenfelder | |
| 2004/0157293 A1 | 8/2004 | Evans et al. | |
| 2005/0064511 A1 | 3/2005 | Buechler et al. | |
| 2005/0244902 A1 | 11/2005 | Gotze et al. | |
| 2005/0244904 A1 | 11/2005 | Ng | |
| 2006/0234315 A1 | 10/2006 | MacFadyen et al. | |
| 2008/0312179 A1 | 12/2008 | Pecker | |

FOREIGN PATENT DOCUMENTS

| | | |
|---|---|---|
| WO | 2006/007667 A1 | 1/2006 |
| WO | 2006/131529 A1 | 12/2006 |
| WO | 2009/004315 A1 | 1/2009 |

OTHER PUBLICATIONS

Solberg, Approved recommendation on the theory of reference values, Part 5, Statistical treatment of collected reference values, Determination of reference limits, J. Clin. Chem. Clin. Biochem., 1987, 645-656, 25.

Squire et al., N-terminal pro-atrial natriuretic peptide (N-ANP) and N-terminal pro-B-type natriuretic peptide (N-BNP) in the prediction of death and heart failure in unselected patients following acute myocardial infarction, Clin. Sci. (Lond.), 2004,309-316, 107(3).

Stewart (Ed.), Solid-Phase Peptide Synthesis, 1969, WH Freeman Co., San Francisco, CA (Table of Contents).

Summah et al., Biomarkers: A Definite Plus in Pneumonia, Mediators Inflamm. 2009, 1-9, 675753.

Suresh et al., Bi-specific monoclonal antibodies from hybrid hybridomas, Methods Enzymol., 1986, 210-228, 121.

Tapanainen et al., Natriuretic peptides as predictors of non-sudden and sudden cardiac death after acute myocardial infarction in the beta-blocking era, J. Am. Coll. Cardiol., 2004, 757-763, 43(5).

Tatusov et al., A Genomic Perspective on Protein Families, Science, 1997, 631-637, 278(5338).

Tatusova et al., BLAST 2 Sequences, a new tool for comparing protein and nucleotide sequences, FEMS Microbial Lett., 1999, 247-250, 174(2).

Thibault et al., NH2-terminal fragment of rat pro-atrial natriuretic factor in the circulation: identification, radioimmunoassay and half-life, Peptides, 1988, 47-53, 9(1).

Thomas, Hybridization of denatured RNA and small DNA fragments transferred to nitrocellulose, Proc. Natl. Acad. Sci. USA, 1980, 5201-5205, 77(9).

Thompson et al., CLUSTAL W: improving the sensitivity of progressive multiple sequence alignment through sequence weighting, position-specific gap penalties and weight matrix choice, Nucleic Acids Res., 1994, 4673-4680, 22(22).

Thygesen et al., Universal Definition of Myocardial Infarction, Circulation, 2007, 2634-2653, 116(22).

Toma et al., Recognition of Human Proinsulin Leader Sequence by Class I-Restricted T-Cells in HLA-A*0201 Transgenic Mice and in Human Type 1 Diabetes, Diabetes, 2009, 394-402, 58(2).

Triglia et al., A procedure for in vitro amplification of DNA segments that lie outside the boundaries of known sequences, Nucleic Acids Res., 1998, 8186, 16(16).

Troughton et al., Plasma B-type natriuretic peptide levels in systolic heart failure: Importance of left ventricular diastolic function and right ventricular systolic function, J. Am. Coll. Cardiol., 2004, 416-422, 43(3).

Troughton et al., Treatment of heart failure guided by plasma amino-terminal brain natriuretic peptide (N-BNP) concentrations, Lancet, 2000, 1126-1130, 355(9210).

Van Erp et al., Application of a Sol Particle Immunoassay to the Dertimination of Affinity Constants of Monoclonal Antibodies, J. Immunoassay, 1991, 425-443, 12(3).

Vaughn et al., Human antibodies by design, Nat. Biotechnol., 1998, 535-539, 16(6).

Verhoeyen et al., Reshaping Human Antibodies: Grafting an Antilysozyme Activity, Science, 1988, 1534-1536, 239 (4847).

Viljoen et al., Molecular diagnostic PCR handbook, 2005, Springer (Table of Contents).

Waiker et al., Imperfect Gold Standards for Kidney Injury Biomarker Evaluation, J. Am. Soc. Nephrol., 2012, 13-21, 23(1).

Walker (Ed.), Protein Protocols Handbook, 2nd Ed., 2002, Humana Press, Totowa, NJ (Table of Contents).

Ward et al., Binding activities of a repertoire of single immunoglobulin variable domains secreted from Escherichia coli, Nature, 1989, 544-546, 341(6242).

Weir (Ed.), Handbook of Experimental Immunology, 4th Ed., 1986, vol. 1, Blackwell Scientific Publications, Oxford (Table of Contents).

Werno et al., Laboratory diagnosis of invasive pneumococcal disease, Clin. Infect. Dis., 2008, 926-932, 46(6).

Wheeler et al., Laboratory Diagnosis of Invasive Pneumococcal Disease, Nucleic Acids Res., 2001, 11-16, 29(1).

Wilson et al., Simplified conjugation chemistry for coupling peptides to F(ab') fragments: autologous red cell agglutination assay for HIV-1 antibodies, J. Immunol. Methods, 1994, 267-273, 175(2).

Yarmush et al., Coupling of antibody-binding fragments to solid-phase supports: site-directed binding of F(ab') 2 fragments, J. Biochem. Biophys. Methods, 1992, 285-297, 25(4).

Zapata et al., Engineering linear F(ab')2 fragments for efficient production in Escherichia coli and enhanced antiproliferative activity, Protein Eng., 1995, 1057-1062, 8(10).

Zola (Ed.), Using Monoclonal Antibodies: Soluble Antigens, Monoclonal Antibodies: A Manual of Techniques, 1987, 147-158, Ch. 6, CRC Press, Inc.

Hoogenboom et al.,Human antibodies from synthetic repertoires of germline VH gene segments rearranged in vitro, J. Mol. Biol., 1992, 381-388, 227(2).

Howard et al. (Eds.), Making and Using Antibodies: A Practical Handbook, 2007, CRC Press (Table of Contents).

Huang, On Global Sequence Alignment, Comput. Appl. Biosci., 1994, 227-235, 10(3).

Hunt et al., Immunoreactive amino-terminal pro-brain natriuretic peptide (NT-PROBNP): a new biomarker of cardiac impairment, Clin. Endocrinol. (Oxf)., 1997, 287-296, 47(3).

Huston et al., Protein engineering of antibody binding sites: Recovery of specific activity in an anti-digoxin single-chain Fv analogue produced in Escherichia coli, Proc. Natl. Acad. Sci. USA, 1988, 5879-5883, 85(16).

Jain, Current Status of Fluorescent In Situ Hybridization, Med. Device Technol., 2004, 14-17, 15(4).

Jernberg et al., N-Terminal Pro Brain Natriuretic Peptide on Admission for Early Risk Stratification of Patients With Chest Pain and No ST-Segment Elevation, J. Am. Coll. Cardiol., 2002, 437-445, 40(3).

Jones et al., Replacing the complementarity determining regions in a human antibody with those from a mouse, Nature, 1986, 522-525, 321(6069).

Jung et al., Elevated concentrations of cardiac troponins are associated with severe coronary artery calcification in asymptomatic haemodialysis patients, Nephrol. Dial. Transplant, 2004, 3117-3123, 19(12).

Klee, Interferences in hormone immunoassays, Clin. Lab. Med., 2004, 1-18, 24(1).

Kohler et al., Continuous cultures of fused cells secreting antibody of predefined specificity, Nature, 1975, 495-497, 256(5517).

Kunkel, Rapid and efficient site-specific mutagenesis without phenotypic selection, Proc. Natl. Acad. Sci. USA, 1985, 488-492, 82(2).

Lindahl et al., High Proinsulin Concentration Precedes Acute Myocardial Infarction in a Nondiabetic Population, Metabolism, 1999, 1197-1202, 48.

Lundblad (Ed.), Techniques in Protein Modification Edition: 2, 1995, CRC Press, (Table of Contents).

Lutz et al., The distribution of two hnRNP-associated proteins defined by a monoclonal antibody is altered in heat-shocked HeLa cells, Exp. Cell. Res., 1988, 109-124, 175(1).

Mandell, Epidemiology and etiology of community-acquired pneumonia, Infect. Dis. Clin. North Am., 2004, 761-776, 18(4).

(56) References Cited

OTHER PUBLICATIONS

Martoglio et al., Signal sequences: more than just greasy peptides, Trends Cell. Biol., 1998, 410-415, 8(10).
Matteucci et al., Synthesis of Deoxyoligonucleotides on a Polymer Support, J. Am. Chem. Soc., 1981, 3185-3191, 103(11).
Mehra et al., Usefulness of elevated B-type natriuretic peptide to predict allograft failure, cardiac allograft vasculopathy and survival after heart transplant, Am. J. Cardiol. 2004, 454-458, 94(4), Pubmed Abstract PMID 15325298.
Merrifield, Solid Phase Peptide Synthesis. I. The Synthesis of a Tetrapeptide, J. Am. Chem. Soc. 1963, 2149-2154, 85(14).
Miller et al. (Eds.), Gene Transfer Vectors for Mammalian Cells, 1987, Cold Springs Harbor, NY (Table of Contents).
Milstein et al., Hybrid hybridomas and their use in immunohistochemistry, Nature, 1983,537-539, 305(5934).
Morrison et al., Chimeric human antibody molecules: Mouse antigen-binding domains with human constant region domains, Proc. Natl. Acad. Sci. USA, 1984, 6851-6855 81(21).
Muller et al. (Eds.), Microarray Technology and its Application, 2005, Springer (Table of Contents).
Mullis et al. (Eds.), The Polymerase Chain Reaction, 1994, Birkhauser (Table of Contents).
Munson et al., LIGAND: A Versatile Computerized Approach for Characterization of Ligand-Binding Systems, Anal. Biochem., 1980, 220-239, 107(1).
Murdoch et al., Breathing New Life into Pneumonia Diagnostics, J. Clin. Micro., 2009, 3405-3408, 47(11).
Naghavi et al., From Vulnerable Plaque to Vulnerable Patient : A Call for New Definitions and Risk Assessment Strategies: Part I, Circulation, 2003, 1664-1672, 108(14).
Needlemen et al., A General Method Applicable to the Search for Similarities in the Amino Acid Sequence of Two Proteins, J. Mal. Biol., 1970, 443-453, 48.
Nelson et al., A computer program for calculating antibody affinity constants , Comput. Methods Programs Biomed., 1988, 65-68, 27(1).
Neuberger, Generating high-avidity human Mabs in mice, Nat. Biotechnol., 1996, 826, 14(7).
Ng et al., Biomedical applications of protein chips, J. Cell. Mol. Med., 2002, 329-340, 6(3).
Nielsen et al., Sequence-Selective Recognition of DNA by Strand Displacement with a Thymine-Substituted Polyamide, Science, 1991, 1497-1500, 254(5037).
NIH Guide, Molecular and Physical Characterization of the Vulnerable Plaque, 1997, 26(37).
Notredame et al., T-Coffee: A Novel Method for Fast and Accurate Multiple Sequence Alignment, J. Mol. Biol., 2002, 205-217, 302(1).
Omland et al., N-Terminal Pro-B-Type Natriuretic Peptide and Long-Term Mortality in Acute Coronary Syndromes, Circulation, 2002, 2913-2918, 106(23).
Omland et al., Plasma brain natriuretic peptide as an indicator of left ventricular systolic function and long-term survival after acute myocardial infarction. Comparison with plasma atrial natriuretic peptide and N-terminal proatrial natriuretic peptide, Circulation, 1996, 1963-1969, 93(11).
Paul (Ed.), Fundamental Immunology, 2nd ed., 1989, Raven Press, NY (Table of Contents).
Pemberton et al., Deconvolution Analysis of Cardiac Natriuretic Peptides During Acute Volume Overload, Hypertension, 2000, 355-359, 36(3).
Pluckthun, Antibodies in *Escherichia coli*, in Rosenburg et al. (Eds.), The Pharmacology of Monoclonal Antibodies, 1994, 113, 269-315, Ch. 11, Springer-Verlag.
Poykko et al., Low plasma ghrelin is associated with insulin resistance, hypertension, and the prevalence of type 2 diabetes, Diabetes, 2003, 2546-2553, 52(10).
Raju et al., T Cell Recognition of Human Pre-Proinsulin Peptides Depends on the Polymorphism at HLA DQ Locus: A Study Using HLA DQ8 and DQ6 Transgenic Mice, Hum. Immunol., 1997, 21-29, 58(1).

Reyzer et al., MALDI Mass Spectrometry for Direct Tissue Analysis: A New Tool for Biomarker Discovery, J. Proteome Res., 2005, 1138-1142, 4(4).
Rice et al., EMBOSS: The European Molecular Biology Open Software Suite, Trends Genet., 2000, 276-277, 16(6).
Richards et al., Antecedent hypertension and heart failure after myocardial infarction, J. Am. Coll. Cardiol., 2002, 1182-1188, 39(7).
Richards et al., Plasma N-Terminal Pro-Brain Natriuretic Peptide and Adrenomedullin : New Neurohormonal Predictors of Left Ventricular Function and Prognosis After Myocardial Infarction, Circulation, 1998, 1921-1929, 97(19).
Riechmann et al., Reshaping human antibodies for therapy, Nature, 1988, 323-327, 332(6162).
Ronco et al., Cardiorenal Syndrome, J. Am. Coll. Cardiol., 2008, 1527-1539, 52(19).
Sambrook et al. (Eds.), Molecular Cloning, A Laboratory Manual, 2nd Ed., 1989, Cold Spring Harbor Press (Table of Contents).
Schuetz et al., Procalcitonin and other biomarkers to improve assessment and antibiotic stewardship in infections—hope for hype?, Swiss Med. Wkly., 2009, 318-326, 139(23-24).
Abbott Press Release, New Point of Care Test Helps Physicians Quickly, Accurately Assess Difficult-to-Diagnose Heart Failure at Patient's Bedside, Jul. 26, 2006, retrieved online Dec. 13, 2007at URL: http://www.abbott.com/global/url/pressRelease/en_US/60.5:5/Press_Release-0339.htm.
Agrawal (Ed.), Protocols for Oligonucleotides and Analogs, Synthesis and Properties, 1993, vol. 20, Humana Press Inc., NJ (Table of Contents).
Altschul et al., Gapped BLAST and PSI-BLAST: a new generation of protein database search programs, Nucleic Acid Res., 1997, 3389-3402, 25(17).
Antman et al., Acute Myocardial Infarction in Braunwald et al. (Eds.), Heart disease: a textbook of cardiovascular medicine, 6th ed., 2001, 1114-1231, vol. 2, Ch. 35.
Apple et al., National Academy of Clinical Biochemistry and IFCC Committee for Standardization of Markers of Cardiac Damage Laboratory Medicine Practice Guidelines: Analytical Issues for Biochemical Markers of Acute Coronary Syndromes, Circulation, 2007, e352-e355, 115(13).
Atherton et al. (Eds.), Solid Phase Synthesis: a practical approach, 1989, IRL Oxford Press, Oxford, England (Table of Contents).
Bairoch et al., PROSITE: recent developments, Nucleic Acids Res., 1994, 3583-3589, 22(17).
Bartlett, Decline in Microbial Studies for Patients with Pulmonary Infections, Clin. Infect. Dis., 2004, 170-172, 39(2).
Baxevanis, The Molecular Biology Database Collection: an updated compilation of biological database resources, Nucleic Acids Res., 2001, 1-10, 29(1).
Bennet et al., The risk of myocardial infarction is enhanced by a synergistic interaction between serum insulin and smoking, Eur. J. Endocrinol., 2002, 641-647, 147(5).
Bolton et al., A General Method for the Isolation of RNA Complementary to DNA, Proc. Natl. Acad. Sci., 1962, 1390-1397, 48(8).
Bowie et al., Deciphering the message in Protein Sequences: Tolerance to Amino Acid Substitutions, Science, 1990, 1306-1310, 247(4948).
Braud et al., HLA-E binds to natural killer cell receptors CD94/NKG2A, B and CNature, 1998, 795-799, 391(6669).
Brennan et al., Preparation of bispecific antibodies by chemical recombination of monoclonal immunoglobulin G1fragments, Science, 1985, 81-83, 229(4708).
Centers for Disease Control and Prevention, Pneumonia FastStats Sheet, Jan. 2012.
Chang et al., Novel strategy for identification of candidate cytotoxic T-cell epitopes from human preproinsulin, Tissue Antigens, 2003, 408-417, 62(5).
Chenna et al., Multiple Sequence Alignment with the Clustal series of programs, Nucl. Acids Res., 2003, 3497-3500, 31(13).
Clackson et al., Making antibody fragments using phage display libraries, Nature, 1991, 624-628, 352(6336).

(56) References Cited

OTHER PUBLICATIONS

Cohen, Nonchromosomal Antibiotic Resistance in Bacteria: Genetic Transformation of *Escherichia coli* by R-Factor DNA, Proc. Natl. Acad. Sci. USA, 1972, 2110-2114, 69(8).

Coligan et al.(Eds.), Current Protocols in Immunology vol. 1, 1991, Wiley-Interscience, New York, NY, USA (Table of Contents Only).

Congia et al., T cell epitopes of insulin defined in HLA-DR4 transgenic mice are derived from preproinsulin and proinsulin, Proc. Natl. Acad. Sci. USA, 1998, 3833-3838, 95(7).

Cwirla et al., Peptides on phage: A vast library of peptides for identifying ligands, Proc. Natl. Acad. Sci. USA, 1990, 6378-6382, 87(16).

Dale et al. (Eds.), From Genes to Genomes: Concepts and Applications of DNA Technology, Ed. 2, 2007, Wiley, NY (Table of Contents).

Davies, Concepts, in Wild (Ed.), The Immunoassay Handbook. 3rd edition, 2005, 103 and 121-126, Ch. 6, Elsevier Ltd.

Deutscher (Ed.), Methods in Enzymology, 1990, 182 (Table of Contents).

Devlin et al., Random Peptide Libraries: A Source of Specific Protein Binding Molecules, Science, 1990, 404-406, 249(4967).

Dieguez et al., Ghrelin: a step forward in the understanding of somatroph cell function and growth regulation, Eur. J. Endocrinol., 2000, 413-417, 142(5).

Ducimetiere et al., Relationship of Plasma Insulin Levels to the Incidence of Myocardial Infarction and Coronary Heart Disease Mortality in a Middle-aged Population, Diabetologia, 1980, 205-210, 19(3).

Evertsen et al., Diagnosis and management of pneumonia and bronchitis in outpatient primary care practices, Prim. Care Resp. J., 2010, 237-241, 19(3).

Falquet et al., The PROSITE database, it's status in 2002, Nucleic Acids Res., 2002, 235-238, 30(1).

Feng et al., Progressive sequence alignment as a prerequisite to correct phylogenetic trees, J. Mol. Evol., 1987, 351-360, 25(4).

Fischer et al., A readers' guide to the interpretation of diagnostic test properties: clinical example of sepsis, Intensive Care Med., 2003, 1043-1051, 29(7).

Freshney (Ed.), Culture of Animal Cells, 2nd Ed., 1987, Alan R. Liss, Inc., NY (Table of Contents).

Frohman, Rapid amplification of complementary DNA ends for generation of full-length complementary DNAs: Thermal race, Methods Enzymol., 1993, 340-356, 218.

Gait (Ed.), Oligonucleotide Synthesis: A Practical Approach, 1984, IPL Press, Oxford, Washington DC (Table of Contents).

Garcia et al., Ghrelin and Cardiovascular health, Curr. Opin. Pharmacol., 2006, 142-147, 6(2).

Gennis et al., Clinical Criteria for the Detection of Pneumonia in Adults: Guidelines for Ordering Chest Roentgenograms in the Emergency Department, J. Emerrg. Med., 1989, 263-268, 7(3).

Giesen et al., A formula for thermal stability (Tm) prediction of PNA/DNA duplexes, Nucleic Acids Res., 1998, 5004-5006, 26(21).

Gilchrist et al., Immunoneutralization of Growth Differentiation Factor 9 Reveals It Partially Accounts for Mouse Oocyte Mitogenic Activity, Biology and Reproduction, 2004, 732-739, 71(3).

Golemis (Ed.), Protein-protein Interactions: A Molecular Cloning Manual, 2002, Cold Springs Harbor, NY (Table of Contents).

Gutierrez-Marcos et al., Atrial natriuretic peptide in patients with accute myocardial infacrtion without functional heart failure, Eur. Heart J., 1991, 503-507, 12(4).

Harlow et al. (Ed.), Using Antibodies: A Laboratory Manual, 1999, Cold Spring Harbor Publications, NY (Table of Contents).

Harlow et al. (Eds.), Antibodies, A Laboratory Manual, 1988, 92-117, Ch. 5, Cold Spring Harbor Publications, NY.

Harlow et al. (Eds.), Antibodies: A Laboratory Manual, 1988, Cold Spring Harbor Press, NY (Table of Contents).

Hermanson (Ed.), Bioconjugate Techniques, 1996, Academic Press, San Diego, CA (Table of Contents).

Hess et al., N-terminal pro-brain natriuretic peptide (NT-proBNP) in healthy blood donors and in patients from general practitioners with and without a diagnosis of cardiac arrest, Clin. Lab. 2005, 167-172, 51(3-4), Pubmed Abstract PMID 15819172.

Hindiyeh et al., Evaluation of the Prodesse Hexaplex Multiplex PCR Assay for Direct Detection of Seven Respiratory Viruses in Clinical Specimens, Am. J. Clin. Pathol., 2001, 218-224, 116(2).

Hofmann et al., The PROSITE database, it's status in 1999, Nucleic Acids Res., 1999, 215-219, 27(1).

Hofmann, Gene Expression Profiling by Microarrays: Clinical Implications, 2006, Cambridge University Press (Table of Contents).

Holliger et al., "Diabodies": Small bivalent and bispecific antibody fragments, Proc. Natl. Acad. Sci. USA. 1993, 6444-6448, 90(14).

\* cited by examiner

Sequences of EPO and CNP signal peptides
(single letter amino acid notation)

EPO MGVHECPAWLWLLLSLLSLPLGLPVLG
CNP MHLSQLLACALLLTLLSLRPSEA

FIG. 1

| Peptide cross reactivity data for EPOsp and CNPsp antisera (%) | |
|---|---|
| proBNP(1-13) | <0.003 |
| proBNP(1-76) | <0.01 |
| proANP(1-30) | <0.009 |
| Insulin | <0.003 |
| IGF-I | <0.002 |
| IGF-II | <0.006 |
| ANP | <0.008 |
| BNP | <0.009 |
| Endothelin 1 | <0.006 |
| Angiotensin II | <0.003 |
| Angiotensin(1-7) | <0.01 |
| Urotensin II | <0.003 |
| CNP | <0.006 |
| Ghrelin | <0.007 |
| C-Ghrelin | <0.01 |
| proCNP(1-15) | <0.008 |
| Adrenomedullin | <0.01 |
| Urocortin I | <0.01 |
| Urocortin II | <0.01 |
| BNP-SPn(1-10) | <0.001 |
| ANP-SPc(16-25) | <0.001 |
| ANP-SPn(1-10) | <0.001 |
| INS-SPn(1-9) | <0.001 |
| Ghrelin-SP(1-9) | <0.002 |
| Clopidigrel | 0 |
| Morphine | 0 |
| Aspirin | 0 |

FIG. 6

SIGNAL BIOMARKERS

RELATED APPLICATION

This application is a divisional application of and claims the benefit of and priority to U.S. patent application Ser. No. 13/186,447, filed on 19 Jul. 2011, now issued as U.S. Pat. No. 9,103,840, issued 11 Aug. 2015, which claims priority to U.S. provisional patent application Ser. No. 61/365,677, filed on 19 Jul. 2010, which is commonly owned with the instant application and is herein incorporated by reference in its entirety for any and all purposes.

SEQUENCE LISTING

The instant application contains a Sequence Listing which has been submitted in ASCII format via EFS-Web and is hereby incorporated by reference in its entirety. Said ASCII copy, created on 1 Sep. 2015, is named OTA1001CT.txt and is 1,456 bytes in size.

FIELD

This invention relates to diagnostics and related technologies, including diagnostics relating to C-type natriuretic and erythropoietin signal peptides, and kits, uses and applications therefor.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

Acute coronary syndromes (ACS) encompass a wide spectrum of cardiac ischemic events ranging from unstable angina through to acute myocardial infarction (AMI). AMI presents as the most serious of these events and therefore requires rapid and accurate diagnosis. Patients who present with two or more of the described features (a history of ischemic chest discomfort, evolutionary changes on serial electrocardiogram (ECG) traces and a rise and fall in plasma cardiac biomarkers) are clearly identified as undergoing AMI.[1] However, a significant proportion of patients (40%-50%) who present with suspected AMI do not have serial changes on ECG, or typical symptoms thus placing heavy emphasis on biomarker analysis for accurate diagnosis.[1,2] Accurate early diagnosis of myocardial infarction facilitates prompt introduction of reperfusion treatment, including effective percutaneous or thrombolytic revascularisation and adjunctive anticoagulant and anti-platelet therapy. Such treatments are progressively less effective at reducing mortality and morbidity with each hour of delay in diagnosis and management.[3-6] Given the need for accelerated decision-making in this clinical situation, there is considerable interest in the identification of biomarkers, particularly circulating biomarkers, that provide an early and specific diagnosis of acute cardiac syndromes and disorders, particularly AMI.[1] Proposed biomarkers include creatine kinase-MB (CK-MB), troponin T (TnT), troponin I (TnI) BNP, N-BNP (also known as NP-BNP), BNP signal peptide (BNP-SP) and myoglobin. Time to detectable or abnormal elevation of plasma cardiac biomarkers, however, can be from up to 6 hours (myoglobin, CK-MB) to 12 hours or more (TnT, TnI, BNP, N-BNP) with peak levels often not occurring until 24-48 hours after onset of injury, imposing a window of delay upon precise diagnosis and treatment.[3-6] Furthermore, both myoglobin and CK-MB are non-specific and can be secreted from extra-cardiac sources, especially during trauma or surgery.[1] A need exists for a marker or suite of markers that provide early and specific information about acute cardiac syndromes and disorders such as acute cardiac injury, particularly within the first few hours of clinical presentation.

There is also a need for means to monitor vascular vulnerable plaques, which provide the substrate for acute cardiac events. Atherosclerosis is a major health problem with an annual mortality of 500,000 deaths in the United States alone. It is currently accepted that acute coronary syndromes are most commonly the result of disruption of atheromatous vulnerable plaques that are angiographically modest in severity. "Vulnerable plaque" is used to refer to a subgroup of modestly stenotic but unstable plaques that are prone to rupture and, as a result, cause sudden cardiac arrest. While coronary angiography is widely used to illustrate and monitor luminal narrowing of the coronary artery, it is unable to provide selective identification of vulnerable plaques. Most of the alternative approaches to identify vulnerable plaques are based on invasive endovascular approaches. Therefore, the development of noninvasive technology which enables vulnerable plaques to be distinguished from stable ones is critical and urgently needed to reduce the morbidity and mortality of atherosclerotic patients. It would be highly desirable if methods and devices were available to detect the unstable atherosclerotic plaque, independent of the degree of luminal diameter narrowing, and treat it before unstable angina and/or acute myocardial infarction and their consequences occur.[7]

According to the National Institutes of Health (Program Announcement PA-09-196, "Ancillary Studies of Acute Kidney Injury, Chronic Kidney Disease, and End Stage Renal Disease Accessing Information from Clinical Trials, Epidemiological Studies, and Databases"), the public health and economic burden of chronic kidney disease in the United States is substantial. Diabetes and hypertension are the main causes of chronic kidney disease. The number of new cases of end-stage kidney disease in 2006 exceeded 110,000 and the number of patients undergoing treatment was over 500,000. As the United States population continues to age it is anticipated that the number of new cases of end-stage kidney disease will also increase. It has been estimated that approximately 26,000,000 people have chronic kidney disease in the US. Acute renal failure in hospitalized patients is also a significant problem in the United States, ranging from 1-15% of hospitalized patients. Medical management of acute renal failure has traditionally consisted primarily of supportive care, with renal replacement therapy for the most severe cases. Despite such interventions in acute renal failure, however, mortality rates in affected patients remain very high (>50% in some series).

Similarly, chronic renal failure (CRF) has high mortality and morbidity, for which there is no specific therapy except supportive care.[8] Histologically, ischemic CRF is characterized by acute tubular necrosis; however a major limitation in approaching the disease is the lack of clinically feasible diagnostics for early detection. Early identification of chronic renal disease and timely detection of progression are challenges facing the global nephrology community, especially since a number of promising primary and secondary interventions to decelerate progression are available. In order to control costs, physicians will need to decrease progression rates of chronic renal disease to end-stage renal disease (ESRD). Current markers of kidney disease and kidney disease progression are the serum creatinine and urinary protein concentration, including microalbuminuria.[8] The slope of the decrease in glomerular filtration rate (GFR) has been demonstrated to predict the timing of ESRD, and the level of proteinuria has been shown in multiple studies to correlate with kidney disease progression rates. However, their ability to recognize early kidney disease is limited. Serum creatinine concentration is dependent on the subject's age, gender, race, muscle mass, weight, degree of physical exertion, and various medications and correct interpretation of kidney function based on serum creatinine requires complex formulas. Although urinary protein is sensitive for progressive renal disease, its appearance occurs after significant renal damage has already occurred. For maximum usefulness, a biomarker of early and/or progressive kidney damage should become positive at the earliest possible point, preferably at that point that kidney damage begins to occur. There remains a strong need for discovery and validation of relevant markers, in particular for early detection.[8]

A continuing problem for the World Anti-Doping Agency is the misuse of peptide/protein hormones such as erythropoietin (EPO) as performance enhancing agents by athletes. Currently, blood and urine samples are analyzed by electrophoretic or immunoassay methodologies for the presence of prohibited substances. Aside from any inherent technical issues, these determinations must account for accepted physiological levels of endogenous peptide hormones as well as determining the presence of their synthetic or recombinant forms. However it is also recognized that for some hormones in this group, newer generations of their synthetic or recombinant form have also rendered their detection more difficult when they are misused in sport, and that this issue is further complicated by (1) technological developments in the construction of synthetic or recombinant EPO, (2) controlled administration at time-points to avoid detection, (3) resultant difficulties in confirming substance levels that exceed the accepted norm, and (4) indeterminate recordings that reflect protein variability in non-specific binding of secondary antibodies (particularly in urine concentrates) and the non-specific enzymatic-induced band shifts in iso-electric tests.

Embodiments of the present invention relate to the discovery of new early markers for diagnostics, including for use in the evaluation, diagnosis and prognosis of, for example, acute coronary syndromes, acute and chronic kidney disorders and injuries, and vulnerable plaque, as well as for use in the detection of EPO doping, for example, by athletes.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

Applicant has discovered signal peptide fragments of C-type natriuretic peptide (CNPsp) and erythropoietin (EPOsp). Applicant has also discovered that these signal peptide fragments are detectable by assay of biological samples, including by assay of samples of biological material that contain material released into the circulation.

The invention relates to signal peptides and signal peptide fragments of C-type natriuretic peptides and erythropoietins, and to methods for their detection (including detection of EPOsp and/or CNPsp and EPOsp and/or CNPsp fragment immunoreactivity), for example, as well as binding agents and assays useful therefor. The invention also relates to and their use in the prognosis, diagnosis and monitoring of biological events or disorders or states which result in their release into body fluids that can be sampled. Examples of biological events, disorders and states for prognosis, diagnosis and monitoring include acute and chronic cardiovascular disorders, vulnerable atherosclerotic plaque, congestive heart failure, cardiac arrhythmia, acute coronary syndromes, chronic arterial disease, acute and chronic kidney diseases disorders, injuries and conditions.

The use and measurement of EPOsp and/or CNPsp immunoreactivity, an EPOsp and/or CNPsp, or fragments, including immunoreactive peptide fragments, of EPOsp and CNPsp, provides superior detection and discriminatory capabilities compared with existing standard markers. In this regard, the much quicker time to reach peak levels in blood and the specific nature of each marker to the condition is noted. The latter arises from the organ specific location of each signal peptide fragment. Thus, EPOsp is specifically released from kidney, whereas CNP is released from the heart and blood vessels. Furthermore, because signal peptides have a shorter half life in blood compared with existing markers, they have the capacity to rise and fall more quickly, detecting underlying active disease. This cannot be said for existing markers, which have long half lives and therefore, possess blood levels which do not respond as rapidly to active disease.

Human EPOsp has the sequence MGVHECPAWL-WLLLSLLSLPLGLPVLG (SEQ ID NO:1)

Human EPOsp fragments include, for example, EPOsp (1-9) and EPOsp(18-27), which may be written as follows:

```
                                        (SEQ ID NO: 2)
            MGVHECPAW (SEQ ID NO: 3)
            SLPLGLPVLG
```

Human CNPsp has the sequence MHLSQ LLACA LLLTL LSLRP SEA (SEQ ID NO:4).

Human CNPsp fragments include, for example, CNPsp (1-13) and CNPsp(14-23), which may be written as follows:

```
                                        (SEQ ID NO: 5)
            MHLSQLLACALLL (SEQ ID NO: 6)
            TLLSLRPSEA
```

Animal analogs of these signal peptides and fragments, as well as variants thereof useful to prepare binding agents to these human and animal signal peptides and fragments are within the invention.

The inventions include methods for predicting, diagnosing or monitoring a biological event or disorder in a subject wherein the event correlates with the release of CNPsp or EPOsp or fragments thereof into the circulation, or for evaluation of EPO doping. In one aspect, a method comprises measuring the level of one or more of these signal peptides or fragments in a biological sample from the subject, and comparing the level of the signal peptide fragments with individual or combinatorial levels of said signal peptide fragments from a control or control population (including historical controls) wherein a deviation in the measured level from the control level is indicative of a biological event. The signal peptides themselves may also be measured.

Applicant has also discovered that EPOsp and/or CNPsp fragments can be used to evaluate the presence of acute cardiac syndromes, and that one or more of said EPOsp and/or CNPsp fragments are typically highest in the first few hours following onset of, or at clinical presentation with a suspected acute coronary syndrome.

In a further aspect the present invention provides a method for predicting, diagnosing or monitoring an ACS in a subject, the method comprising measuring the level of EPOsp and/or CNPsp fragments in a biological sample from the subject and comparing the level of said EPOsp and/or CNPsp fragments with the level of said EPOsp and/or CNPsp fragments from one or more controls wherein a measured level of said EPOsp and/or CNPsp fragments higher than the control level is indicative of an ACS.

Elevated levels of EPOsp and/or CNPsp fragments are typically diagnostic of MI and angina.

Elevated levels of EPOsp and/or CNPsp fragments may also be used as a diagnostic for heart failure.

Elevated levels of EPOsp and/or CNPsp fragments may also be used as a diagnostic for vascular disease and/or atherosclerosis. CNPsp, for example, can be elevated by about 50% or more over normal in these conditions.

Elevated levels of CNPsp fragments may also be used for diagnoses of hypertension.

Elevated levels of CNPsp fragments may also be used for diagnoses of syncope, a temporary loss of consciousness and posture usually related to temporary insufficient blood flow to the brain. Syncope most often occurs when the blood pressure is too low (hypotension) and the heart doesn't pump a normal supply of oxygen to the brain.

Elevated levels of EPOsp and/or EPOsp fragments may also be used for evaluation of EPO doping. An EPO/EPOsp immunoreactivity (indicative of an EPOsp and/or an EPOsp fragment or fragments) plasma ratio could be expected to exceed up to 1000:1, for example, particularly during the acute phase of administration.

The inventions also include methods for monitoring a response to treatment of a biological event or disorder, particularly an acute cardiac syndrome in a subject, the method comprising measuring the level of one or more of the signal peptide fragments referenced herein, for example, EPOsp and/or CNPsp fragments, in a biological sample from the subject, preferably before and after treatment, and comparing the level of said fragments with the level of said fragments from a control, wherein a change in the level or measured level (e.g., an historical level or baseline) of fragments from the control level is indicative of a response to the treatment.

The invention also includes methods for diagnosing or evaluating acute and chronic renal disease or renal failure or injury in a subject, wherein measurement of the level of EPOsp shows a negative correlation with GFR (an indicator of renal function). Plasma EPOsp levels, for example, are elevated in patients with chronic renal disease and in those with heart failure compared with normal. The ratio of EPOsp to EPO is about 6 in normal health, and this rises to approximately 10 in renal disease and drops to about 4 in heart failure patients.

The invention also includes methods for predicting, diagnosing or monitoring an acute cardiac syndrome in a subject, the method comprising measuring the level of one or more of EPOsp and/or CNPsp fragments in a biological sample obtained from the subject within about the first 12 hours or more, preferably the first 4-6 hours or less, of onset of, or clinical presentation with an ACS or suspected ACS, comparing the measured level of said one or more of EPOsp and/or CNPsp fragments with the level of one or more of EPOsp and/or CNPsp fragments from a control (e.g., an historical control or known control level), wherein a measured level of one or more of EPOsp and/or CNPsp fragments higher than the control level is indicative of an ACS.

Broadly, the inventions can be used to predict, diagnose or monitor any event in which one or more of EPOsp and/or CNPsp and/or fragments thereof are released from cells, for example, into the circulation or other biological fluid or tissue.

In one embodiment of the methods of the invention, particularly for a cardiovascular or renal disorder, or suspected cardiovascular or renal disorder, the level(s) of one or more of the EPOsp and/or CNPsp and/or fragments thereof is/are measured within about forty-eight hours, about twenty-four hours, about twelve hours, about ten hours, about eight hours, about six hours, about four hours, about two hours, or about one hour, or within about 30 minutes of presentation of the patient with a disorder or suspected disorder.

In one embodiment, the methods of the invention are in vitro methods and the biological sample is blood, plasma, serum, urine, saliva, interstitial fluid or heart tissue.

In one embodiment, the measuring step comprises detecting binding between one or more target fragments and a binding agent that binds said fragment or fragments with desired specificity and selectivity. The measuring step may comprise:
  (a) bringing together a biological sample containing or suspected of containing one or more target fragments with a binding agent or agents, with or without an incubation step; and
  (b) measuring the level of bound target signal peptide(s) or fragment(s).

The binding agent may be, for example, an antibody, or any molecule comprising an antigen-binding fragment thereof. Most commonly, the antibody may be a monoclonal, polyclonal, chimeric or humanized antibody. In one embodiment the antibody is a monoclonal antibody. In another embodiment, the binding agent is, for example, a single chain antibody or scFv. In one embodiment, the anti-fragment binding agent is, for example, an antibody or antigen-binding fragment thereof that recognizes fragments in or obtained from a biological sample.

In another embodiment, the levels of one or more target fragments is/are measured using mass spectroscopy.

One or more of the peptides or peptide fragments corresponding to SEQ ID NOS:1-6 (or non-human analogs or variants thereof), or other signal peptide fragments, may be bound using a binding agent of the invention. Other EPOsp and CNPsp fragments are also within the invention.

The molecules which is/are bound by the binding agent or agents may be the full-length human signal peptide molecules (SEQ ID NOS:1, 4) or an antigenic variant or fragment thereof. In one embodiment, the fragment is at least four contiguous amino acids in length. The binding agent or agents may, for example, bind the N-terminus or the C-terminus of an EPOsp and/or CNPsp. The fragments may, for example, be any of SEQ ID NOS:2, 3, 5 and/or 6.

Binding of one or more of the peptides or peptide fragments corresponding to SEQ ID NOS:1-6 (or non-human analogs or variants thereof), or other signal peptide fragments, may be measured, for example, using antibodies or antibody fragments or other binding agents that are immobilised on a solid phase.

Levels of one or more of the peptides or peptide fragments corresponding to SEQ ID NOS:1-6 (or non-human analogs or variants thereof), or other signal peptide fragments, may usefully be measured by, for example, RIA, ELISA, fluoroimmunoassay, immunofluorometric assay, mass spectrometry or immunoradiometric assay. The methods of the invention include the use of binding agents and assays for one or more of the peptides or peptide fragments corresponding to SEQ ID NOS:1-6 (or non-human analogs or variants thereof), or other signal peptide fragments, in a biological sample from a subject, the assay comprising determining the presence or amount of one or more of the peptides or peptide fragments corresponding to SEQ ID NOS:1-6 (or non-human analogs or variants thereof), or other signal peptide fragments, in the sample using any known methods.

The invention also provides assays, including assays for the uses described herein, for one or more of the peptides or peptide fragments corresponding to SEQ ID NOS:1-6 (or non-human analogs or variants thereof), or other EPOsp and/or CNPsp fragments, comprising, for example:

(a) binding one or more one or more of the peptides or peptide fragments corresponding to SEQ ID NOS:1-6 (or non-human analogs or variants thereof) from a sample; and (b) measuring the level of one or more bound peptides or peptide fragments corresponding to SEQ ID NOS:1-6 (or non-human analogs or variants thereof).

The invention also provides a assay or assays for one or more of the peptides or peptide fragments corresponding to SEQ ID NOS:1, 2, 3, 4, 5 or 6 (or non-human analogs or variants thereof), or other signal peptide fragments, for use in predicting, diagnosing or monitoring biological event or disorder in a subject. In one embodiment, the assay is an in vitro assay.

The invention also includes isolated, substantially purified, or purified, as well as synthetically made, fragments corresponding to, for example, any of SEQ ID NOS:2, 3, 5 and/or 6.

The cardiac-related methods of the invention may further comprise measuring the level of one or more non-EPOsp and non-CNPsp markers of, for example, ACS, and comparing the levels against marker levels from a control wherein a deviation in the measured level from a control level, together with a measured level of one or more of EPOsp and/or CNPsp fragments which is higher than the control level of one or more of EPOsp and/or CNPsp fragments, is predictive or diagnostic of the ACS, or can be used to monitor said ACS. Markers for use in the context of acute coronary syndrome include, for example, troponin T, troponin I, creatine kinase MB, myoglobin, BNP, NT-BNP, BNP-SP, ANP, ANP-SP, LDH, aspartate aminotransferase, and heart specific fatty acid binding protein (H-FABP).

In another aspect, the present invention also provides a binding agent for one or more of the peptides or peptide fragments corresponding to SEQ ID NOS:1-6 (or non-human analogs or variants thereof), or other fragments. In one embodiment, the binding agent of the invention binds one of SEQ ID NOS:2, 3, 5 and/or 6. In another embodiment, the binding agent binds a variant or fragment of one or more of the peptides or peptide fragments corresponding to SEQ ID NOS:1-6 (or non-human analogs or variants thereof), or other signal peptide fragments.

The binding agent is useful in predicting, diagnosing or monitoring a biological event or disorder which correlates with the release of one or more of the peptides or peptide fragments corresponding to SEQ ID NOS:1, 2, 3, 4, 5 or 6 (or non-human analogs or variants thereof), or other signal peptide fragments, including, for example, into the circulation. Such events or disorders include acute cardiac syndromes in a subject.

The invention also provides an anti-EPOsp and/or anti-CNPsp antibody or antigen-binding fragment thereof. The antibody may be a monoclonal, polyclonal, chimeric or humanized antibody, for example. The invention also includes antibodies and binding fragments thereof that bind to EPOsp and/or CNPsp fragments, including fragments identified by SEQ ID NOS:2, 3, 5 and/or 6.

The invention is also directed to the use of a binding agent in the manufacture of a assay for one or more of the peptides or peptide fragments corresponding to SEQ ID NOS:1-6 (or non-human analogs or variants thereof), or other signal peptide fragments, for assessing a biological event or disorder in a subject, or to the use of a binding agent in the manufacture of a prognostic, diagnostic or monitoring tool for assessing a biological event or disorder in a subject and/or the treatment thereof, or for evaluation of EPO misuse or doping. In one embodiment, the event or disorder correlates with the release of one or more of the peptides or peptide fragments corresponding to SEQ ID NOS:1-6 (or non-human analogs or variants thereof), or other signal peptide fragments, into the circulation including from or following a chronic renal disease or injury, heart failure, hypertension, syncope, vascular disease including atherosclerosis, or an acute cardiac syndrome including myocardial infarction and angina, or EPO misuse or doping.

The invention also relates to the use of an antibody or antigen-binding fragment of the invention in the manufacture of a prognostic, diagnostic or monitoring tool for assessing a biological event or disorder which correlates with the release of one or more of the peptides or peptide fragments corresponding to SEQ ID NOS:1-6 (or non-human analogs or variants thereof), or other signal peptide fragments, including, for example, into the circulation including a chronic renal disease or injury, heart failure, hypertension, syncope, vascular disease including atherosclerosis, or an acute cardiac syndrome or disorder including myocardial infarction and angina in a subject.

In one embodiment the prognostic, diagnostic or monitoring tool is calibrated to measure levels of one or more of the peptides or peptide fragments corresponding to any of SEQ ID NOS:1-6 (or non-human analogs or variants thereof), or other signal peptide fragments, in the range of, for example, from 0.1 to 1500 pmol/L, 0.1 to 500 pmol/L, 1 to 300 pmol/L, 10 to 250 or 20 to 150 pmol/L. Furthermore, erythropoietin signal peptides may be found in biological samples, including plasma samples, at levels ranging from about 400 to 4000 pmol/L, about 400 to 200 pmol/L, about 320 to 520 pmol/L, or about 400-420 pmol/L or less. Levels at least as low as 5 pmol/L are detectable. Angiotensin signal peptides may be found in biological samples, including plasma samples, at levels ranging from about 10 to 1000 pmol/L, about 5 to 500 pmol/L, about 1 to 100 pmol/L, or about 0.1 to 10 pmol/L or less. Levels at least as low as 0.1 pmol/L are detectable. C-type natriuretic signal peptides may be found in biological samples, including plasma samples, at levels ranging from about 50 to 1500 pmol/L, about 25 to 750 pmol/L, about 10 to 500 pmol/L, or about 5 to 150 pmol/L or less. Levels at least as low as 2 pmol/L are detectable. Endothelin-1 signal peptides may be found in biological samples, including plasma samples, at levels ranging from about 10 to 200 pmol/L, about 5 to 100 pmol/L, about 10 to 50 pmol/L, or about 1 to 20 pmol/L or less. Levels at least as low as 1 pmol/L are detectable.

In one aspect, the normal level of EPOsp and/or EPOsp fragments, including SEQ ID NOS:1-3 is about 14 to about 90 pmol/L and in one of more of the disease states or conditions referenced herein is about 30 to about 200 pmol/L. Such levels can be measured, for example, in blood or plasma.

In one aspect, the normal level of CNPsp and/or CNPsp fragments, including SEQ ID NOS:4-6 is about 5 to about 15 pmol/L and in one of more of the disease states or conditions referenced herein is about 18 to about 55 pmol/L. Such levels can be measured, for example, in blood or plasma.

In another aspect, the invention provides a kit for predicting, diagnosing or monitoring a biological event or disorder in a subject, the kit comprising a binding agent against a peptide or peptide fragment corresponding to one or more of SEQ ID NOS:1-6 (or non-human analogs or variants thereof), or other signal peptide fragments.

In one embodiment the kit is calibrated to measure levels a peptide or peptide fragment corresponding to any one or more of SEQ ID NOS:1-6 (or non-human analogs or variants thereof), or other signal peptide fragments, in the ranges noted above.

In one embodiment the kit also includes information and/or instructions for carrying out an assay using the binding agent. The kit may also include information and/or instructions for predicting, diagnosing or monitoring a biological event or disorder including one or more of chronic renal disease or injury, heart failure, hypertension, syncope, vascular disease including atherosclerosis, or an acute cardiac syndrome including myocardial infarction and angina in a subject, from the level of one or more of the peptides or peptide fragments corresponding to SEQ ID NOS:1, 2, 3, 4, 5 or 6 (or non-human analogs or variants thereof), or other signal peptide fragments, measured in a biological sample and comparing the measured level to a control level.

The invention also relates to the use of one or more of the peptides or peptide fragments corresponding to SEQ ID NOS:1-6 (or non-human analogs or variants thereof), or other signal peptide fragments, in the preparation of an antibody or binding fragment thereof.

BRIEF DESCRIPTION OF THE DRAWINGS

The invention will now be described with reference to the figures in the accompanying drawings in which FIG. 1 shows the amino acid sequences of EPOsp (SEQ ID NO: 1) and CNPspP (SEQ ID NO: 4) using single letter notation.

FIG. 6 shows a table of cross reactivity data of EPOsp and CNPsp antiserum.

DEFINITIONS

Figure 5:
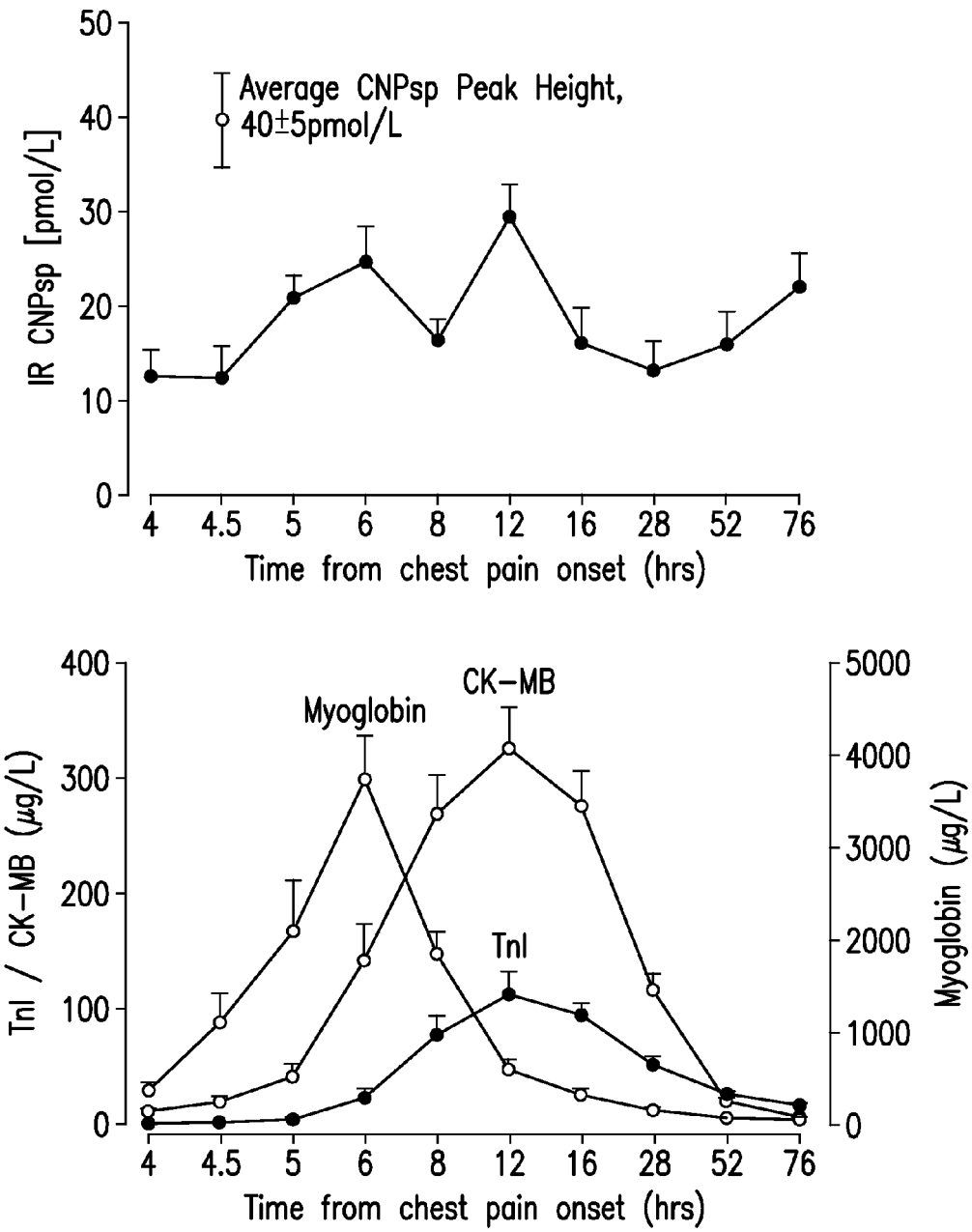
FIG. 5 Immunoassay results showing Upper panel: Serial plasma concentrations of CNPsp(14-23) in 8 patients with documented ST-elevation myocardial infarction (STEMI) from the time of onset of chest pain at hospital emergency department. Lower panel: concomitant TnI, CK-MB and myoglobin plasma levels in the same STEMI patients identified in the upper panel.

Acute coronary syndromes encompasses a wide spectrum of cardiac ischemia events including acute myocardial infarction (AMI) with ST-elevation on presenting ECG, unstable angina, and acute non-ST-elevated myocardial infarction; cardiac ischemia; acute cardiac injury; acute cardiac damage resulting from acute drug toxicity; and acute cardiomyopathies. Full descriptive, definitions of these disorders are found in reference 1. See, e.g., FIG. 5.

Acute (sudden) kidney failure is the sudden loss of the ability of the kidneys to remove waste and concentrate urine without losing electrolytes. There are many possible causes of such kidney damage, including disease and injury. They include acute tubular necrosis; autoimmune kidney disease; decreased blood flow due to very low blood pressure; disorders that cause clotting within the kidney's blood vessels; infections that directly injure the kidney; pregnancy complications; and urinary tract obstruction. Chronic kidney disease is the slow loss of kidney function over time. Symptoms include bloody stools, breath odor, bruising easily, changes in mental status or mood, decreased appetite, decreased sensation, especially in the hands or feet, fatigue, flank pain (between the ribs and hips), hand tremor, high blood pressure, metallic taste in mouth, nausea or vomiting (which may last for days), nosebleeds, persistent hiccups, prolonged bleeding, seizures, slow, sluggish movements, generalized swelling (fluid retention), swelling of the ankle, foot, and leg, and urination changes (decrease in amount of urine, excessive urination at night, and urination stops completely).

Chronic kidney disease (CKD) slowly gets worse over time. In the early stages, there may be no symptoms. The loss of function usually takes months or years to occur. It may be so slow that symptoms do not occur until kidney function is less than one-tenth of normal. The final stage of chronic kidney disease is called end-stage renal disease (ESRD). The kidneys no longer function and the patient needs dialysis or a kidney transplant. Chronic kidney disease and ESRD affect more than 2 out of every 1,000 people in the United States. Diabetes and high blood pressure are the two most common causes and account for most cases. Injuries are another cause. Many other diseases and conditions can damage the kidneys, including problems with the arteries leading to or inside the kidneys; birth defects of the kidneys (such as polycystic kidney disease); some pain medications and other drugs; certain toxic chemicals; autoimmune disorders (such as systemic lupus erythematosus and scleroderma); injury or trauma glomerulonephritis; kidney stones and infection; reflux nephropathy (in which the kidneys are damaged by the backward flow of urine into the kidneys)' and other kidney diseases. Symptoms may include general ill feeling and fatigue, generalized itching (pruritus) and dry skin, headaches, weight loss without trying to lose weight, appetite loss, and nausea. Other symptoms that may develop, especially when kidney function has worsened, include abnormally dark or light skin, bone pain, brain and nervous system symptoms, drowsiness and confusion, problems concentrating or thinking, numbness in the hands, feet, or other areas, muscle twitching or cramps, breath odor, easy bruising, bleeding, or blood in the stool, excessive thirst, frequent hiccups, low level of sexual interest and impotence, menstrual periods stop (amenorrhea), sleep problems, such as insomnia, restless leg syndrome, and obstructive sleep apnea, swelling of the feet and hands (edema), and vomiting, typically in the morning.

A vulnerable plaque is an atheromatous plaque which is particularly prone to produce sudden major problems, such as a heart attack or stroke. Plaque rupture, the most frequent cause of coronary thrombosis, has been implicated in the episodic progression of coronary stenosis as demonstrated by sequential angiography and is often associated with unstable angina, myocardial infarction, and sudden death. Atherosclerotic plaques that are vulnerable to rupture have a dense infiltrate of macrophages and, to a lesser extent, lymphocytes, within a fibrous cap that overlies a crescentic hypocellular mass of lipids. Thus, vulnerable plaque is often characterized as an atheromatous plaque in an arterial wall, which has abundant macrophages, gobs of lipids and cholesterol, and is usually covered by a thin fibrous cap which may rupture. The ruptured plaque results in exposure of blood to the lipid core and other plaque components and is believed to instigate the majority of coronary thrombi. The characterization of these relatively less stenotic plaques prone to erosion or rupture, and the recognition that they contribute to unstable angina and myocardial infarction, has important implications. Early identification of potentially vulnerable plaques may lead to changes in the indications for patients considered for bypass surgery, angioplasty, and other procedures. See "Molecular and Physical Characterization of the Vulnerable Plaque" NIH guide, Volume 26, Number 37, Nov. 7, 1997

The term "antibody" refers to an immunoglobulin molecule having a specific structure that interacts (binds) specifically with a molecule comprising the antigen used for synthesizing the antibody or with an antigen closely related to it. As used herein, the term "antibody" broadly includes full length antibodies and may also include antigen binding fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured. Also included are single chain antibodies, scFvs, and other molecules containing antigen binding constructs. An antibody binds selectively or specifically to an EPOsp and/or CNPsp polypeptide or fragment of the invention if the antibody binds preferentially to the target, including, for example, those having less than about 25%, or less than about 10%, or less than about 1% or less than about 0.1% cross-reactivity with a non-EPOsp and/or non-CNPsp polypeptide or polypeptide fragment. The antibody will have any useful binding affinity binding affinity (dissociation constant (Kd) value), for the antigen or epitope for the uses described and claimed herein. Typical binding affinity may be equal to, for example, $10^{-6}$, or $10^{-7}$M, and more typically at least about $10^{-8}$M, $10^{-9}$M, $10^{-10}$, $10^{-11}$ or $10^{-12}$ M. Binding affinity ay be assessed using surface plasma resonance, or other methods known in the art.

As used herein, an "antigen-binding fragment" or "antibody fragment" means a portion of the intact antibody that preferably retains most or all, or minimally at least one of, the normal functions of that antibody fragment. An antibody fragment, for example, may comprise an Fv region that retains all or most or some of the function of the corresponding Fv region in the intact antibody-antigen binding region. Examples of antibody fragments include Fab, Fab', F(ab')$_2$ and Fv fragments, linear antibodies, diabodies, single chain antibodies (ScFV) and multispecific antibodies.

As used herein, a "monoclonal antibody" means an antibody that is directed against a single target antigen. A monoclonal antibody may be obtained from a population of homogenous or substantially homogenous antibodies wherein each monoclonal antibody is identical and/or bind the same epitope, except for natural mutations which may occur in minor amounts.

An "isolated antibody" is an identified antibody which has been separated or recovered, or both, from a component of its natural environment, for example, separated from other proteins including enzymes and hormones. In one embodiment, the antibody is purified to at least about 95%, about 96% about 97% about 98% or about 99% by weight of antibody. Purity can be determined by the Lowry method, for example. Ordinarily the antibody will be prepared by at least one purification step.

The term "binding agent" as used herein refers to any solid or non-solid material capable of binding an EPOsp and/or CNPsp polypeptides, or a fragment or variant thereof. In one embodiment the term refers to any natural or non-natural molecule that binds to an EPOsp and/or CNPsp polypeptide or a fragment or variant thereof. Examples of binding agents include proteins, peptides, nucleic acids, carbohydrates, lipids, and small molecule compounds.

Biological sample as used herein means any sample derived from a subject to be screened that contains or is suspected of containing a EPOsp and/or CNPsp polypeptide or polypeptide fragment. The sample may be any sample known in the art in which the target can be detected. Included are body fluids such as plasma, serum, blood (including arterial and/or venous samples), urine, saliva, interstitial fluid, synovial, cerebrospinal, lymph, seminal, amniotic, pericardial fluid and ascites, as well as tissues such as cardiac and renal tissues but not limited thereto.

The term "epitope" includes any protein determinant capable of specific binding to an immunoglobulin and/or T cell receptor. That is, a site on an antigen to which antibodies bind or B and/or T cells respond. Epitopic determinants usually consist of chemically active surface groupings of molecules such as amino acids or sugar side chains, and usually have specific three dimensional structural characteristics, and specific charge characteristics. An epitope typically includes 3, 5 or usually 8-10 amino acids. The amino acids may be contiguous, or non-contiguous amino acids juxtaposed by tertiary folding.

Within about 2 or 4 to about 12 hours of the onset of symptoms or clinical presentation includes from 1 minute up to and including about 240 to about 720 or minutes from onset of, or presentation at a medical facility, for example, with ACS, or other disorder or suspected disorder as described herein. Measurements may be made within about 10 hours (from 1 minute up to and including about 600 minutes), within about 8 hours (from 1 minute up to and including about 480 minutes), within about 6 hours (from 1 minute up to and including about 360 minutes), within about 4 hours (from 1 minute up to and including about 240 minutes), within about 2 hours (from 1 minute up to and including about 120 minutes) or within about 1 hour (from 1 minute up to and including about 60 minutes) from onset or presentation, within 5 to about 45 minutes, 15 to about 40 minutes, 20 to about 35 minutes, or within about 25 to 30 minutes of onset or presentation.

A level "higher" or "lower" than a control, or a change or deviation from a control in one embodiment is statistically significant. A higher level, lower level, deviation from, or change from a control level or mean or historical control level can be considered to exist if the level differs from the control level by about 5% or more, by about 10% or more, by about 20% or more, or by about 50% or more compared to the control level. Statistically significant may alternatively be calculated as P<0.05. Higher levels, lower levels, deviation, and changes can also be determined by recourse to assay reference limits or reference intervals. These can be calculated from intuitive assessment or non-parametric methods. Overall, these methods may calculate the 0.025, and 0.975 fractiles as 0.025*(n+1) and 0.975 (n+1). Such methods are well known in the art.[9,10] Presence of a marker absent in a control may be seen as a higher level, deviation or change. Absence of a marker present in a control may be seen as a lower level, deviation or change.

Included are samples from any subjects such as from normal healthy subjects with no clinical history of biological events or disorders, including diabetes or ACS, and subjects with various ACS's including but not limited to acute coronary syndromes: AMI with ST-elevation on presenting ECG, unstable angina, and acute non ST-elevated MI; cardiac ischemia; acute cardiac injury; acute cardiac damage resulting from acute drug toxicity, and acute cardiomyopathies.

The term "cardiomyopathies" as used herein refers to diseases of the myocardium where the myocardium or heart muscle is weakened. This can result in reduced pumping of the heart. Common causes of cardiomyopathies are heart attacks, viral infections, high blood pressure, alcoholism, and autoimmune diseases.

"Biological event or disorder" as used herein refers to a range of events in which EPOsp and/or CNPsp polypeptides or polypeptide fragments is/are released from cells and into, for example, the circulation of a subject, including acute and chronic conditions. Exemplar conditions include acute and chronic kidney disease and cardiovascular disease (including acute coronary syndromes). Examples of chronic conditions are heart failure, AMI and cardiovascular disease, as well as hypertension.

EPOsp and/or CNPsp refer to the complete signal peptide for the human sequence. Also encompassed within the terms EPOsp and/or CNPsp are variants and fragments thereof. In one embodiment an EPOsp and/or CNPsp polypeptide functions as a signal polypeptide, or as an antigenic polypeptide to which an antibody can bind. Variants and fragments of an EPOsp and/or CNPsp include variants and fragments which retain either or both of these functions.

The term "comprising" as used in this specification and claims means "including"; that is to say when interpreting statements in this specification and claims which include "comprising", the features prefaced by this term in each statement all need to be present but other features can also be present. Related terms such as "comprise" and "comprised" are to be interpreted in similar manner.

The term "polypeptide", as used herein, encompasses amino acid chains of any length, including full length sequences in which amino acid residues are linked by covalent peptide bonds. Polypeptides useful in the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof. Polypeptides herein may have chain lengths of at least 4 amino acids, at least 5 amino acids, or at least 6, at least 7, at least 8, at least 9, at least 10, at least 11, at least 12, at least 13, at least 14, at least 15, at least 16, at least 17, at least 18, at least 19, at least 20, at least 21, at least 22, or all 23 amino acids of the full-length EPOsp and/or CNPsp. Reference to other polypeptides of the invention or other polypeptides described herein should be similarly understood.

A "fragment" of a polypeptide is a subsequence of the polypeptide that may be detected using a binding agent. The term may refer to a polypeptide, an aggregate of a polypeptide such as a dimer or other multimer, a fusion polypeptide, a polypeptide fragment, a polypeptide variant, or derivative thereof.

The term "isolated" as applied to the polypeptide sequences disclosed herein is used to refer to sequences that are removed from their natural cellular or other naturally-occurring biological environment. An isolated molecule may be obtained by any method or combination of methods including biochemical, recombinant, and synthetic techniques. The polypeptide sequences may be prepared by at least one purification step.

The term "purified" as used herein does not require absolute purity. Purified refers in various embodiments, for example, to at least about 80%, 85%, 90%, 95%, 98%, or 99% homogeneity of a polypeptide, for example, in a sample. The term should be similarly understood in relation to other molecules and constructs described herein.

As used herein, the term "variant" refers to polypeptide sequences different from the specifically identified sequences, wherein 1 to 6 or more or amino acid residues are deleted, substituted, or added. Substitutions, additions or deletions of one, two, three, four, five or six amino acids are contemplated. Variants may be naturally occurring allelic variants, or non-naturally occurring variants. Variants may be from the same or from other species and may encompass homologues, paralogues and orthologues. In certain embodiments, variants of the polypeptides useful in the invention have biological activities including signal peptide activity or antigenic-binding properties that are the same or similar to those of the parent polypeptides. The term "variant" with reference to polypeptides encompasses all forms of polypeptides as defined herein.

Variant polypeptide sequences exhibit at least about 50%, at least about 60%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to a sequence of the present invention. With regard to polypeptides, identity is found over a comparison window of at least 5 to 7 amino acid positions.

Polypeptide variants also encompass those which exhibit a similarity to one or more of the specifically identified sequences that is likely to preserve the functional equivalence of those sequences, including those which could not reasonably be expected to have occurred by random chance. As discussed above, in the case of EPOsp and/or CNPsp variants function may be as either a signal polypeptide, or antigenic polypeptide, or both.

Polypeptide sequence identity and similarity can be determined in the following manner. The subject polypeptide sequence is compared to a candidate polypeptide sequence using BLASTP (from the BLAST suite of programs, version 2.2.18 [April 2008]]) in bl2seq, which is publicly available from NCBI (ftp://ftp.ncbi.nih.gov/biast/). The default parameters of bl2seq are utilized except that filtering of low complexity regions should be turned off.

The similarity of polypeptide sequences may be examined using the following UNIX command line parameters: bl2seq -i peptideseq1 -j peptideseq2 -F F -p blastp. The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match. Variant polypeptide sequences commonly exhibit an E value of less than $1\times10^{-5}$, less than $1\times10^{-6}$, less than $1\times10^{-9}$, less than $1\times10^{-12}$, less than $1\times10^{-15}$, less than $1\times10^{-18}$ or less than $1\times10^{-21}$ when compared with any one of the specifically identified sequences. Polypeptide sequence identity may also be calculated over the entire length of the overlap between a candidate and subject polypeptide sequences using global sequence alignment programs. EMBOSS-needle (available at http:/www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity. Use of BLASTP is preferred for use in the determination of polypeptide variants according to the present invention.

In one embodiment variants include peptides whose sequence differ from the human signal peptides and fragments herein by one, two, three, four, five, six or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine. Examples of conservative substitutions can also be found in the sequences as shown in the sequence listings whereby the substitutions in different mammalian species compared to the human sequence are shown. Other conservative substitutions are known in the art.

Non-conservative substitutions may also be used and may entail, for example, exchanging a member of one amino acid class (e.g., hydrophobic, neutral hydrophilic, acidic, basic, residues that influence chain orientation, and aromatic) for a member of another class.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

"Subject" as used herein is preferably a mammal and includes human, and non-human mammals such as cats, dogs, horses, cows, sheep, deer, mice, rats, primates (including gorillas, rhesus monkeys and chimpanzees), and other domestic farm or zoo animals. In one embodiment, the mammal is human.

The term "presentation" as used herein refers to presentation of a subject, including, for example, before medical personnel at a medical facility such as a doctor's office, clinic or hospital. Presentation, however, includes presentation of a subject before any person who will use the invention, e.g., paramedic personnel in an ambulance.

The term "treat", "treating" or "treatment" and "preventing" refer to therapeutic or prophylactic measures which alleviate, ameliorate, manage, prevent, restrain, stop or reverse progression of a biological event characterized by a EPOsp and/or CNPsp polypeptide or polypeptide fragment level which shows a deviation from normal control levels, including cardiovascular disease, an ACS, renal disease and AMI, and other disorders and conditions noted herein. The subject may show observable or measurable (statistically significant) reduction in one or more of glucose, lactate, insulin, fatty acids, triglycerides, TnI, TnT, BNP, N-BNP, BNP-SP, ANP, ANP-SP, creatine kinase-MB, myoglobin LDH, aspartate aminotransferase, H-FABP, endothelin, adrenomedullin, rennin, angiotensin II, and other markers.

The term "mass spectrometry" as used herein refers to methods of filtering, detecting, and measuring ions based on their mass to charge ratio. See for example U.S. Pat. Nos. 5,719,060, 6,204,500, 6,107,623, 6,124,137, 6,225,047, 6,268,144, 7,057,165, and 7,045,366. Common mass spectrometry techniques include matrix-assisted laser desorption ionization (MALDI) and surface-enhanced laser desorption ionization (SELDI). Both may be coupled with time of flight analysers (MALDI-TOF and SELDI-TOF) which allow for analysis of analytes at femtomole levels in very short ion pulses.

Versions of SELDI discussed for example in U.S. Pat. Nos. 5,719,600, 6,124,137, and 6,225,047 which are useful in this invention include Surface-Enhanced Affinity Capture (SEAC), Surface-Enhanced Neat Desorption (SEND), and Surface-Enhanced Photolabile Attachment and Release (SEPAR).

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION

It has long been thought that the functional roles of EPOsp and/or CNPsp EPOsp and/or CNPsp were limited to controlling the trafficking of parent molecules in the endoplasmic reticulum. Once this is achieved it has been assumed that the signal peptide is then degraded without ever being secreted from the cell.[12]

The inventors have discovered that EPOsp and/or CNPsp EPOsp and/or CNPsp fragments are available in biological samples and appear, for example, in the circulation.

Additionally the inventors have discovered that EPOsp and CNPsp and fragments thereof are useful as, for example, circulating biomarkers for a range of biological events or disorders.

The use and measurement of immunoreactive signal peptide fragments of EPOsp and/or CNPsp provides superior detection and discriminatory capabilities compared with existing standard markers. In this regard, the much quicker time to reach peak levels in blood and the specific nature of each marker to the condition is noted. With regard to the latter the organ specific location of each signal peptide fragment is also noted. Thus, EPOsp is released from kidney, whereas CNP is released from the heart and blood vessels. Furthermore, because signal peptides have a shorter half life in blood compared with existing markers, they have the capacity to rise and fall more quickly, detecting underlying active disease. This cannot be said for existing markers, which have long half lives and therefore, possess blood levels which do not respond as rapidly to active disease.

In one aspect, the invention provides a method for predicting, diagnosing or monitoring a biological event in a subject wherein the event correlates with the release of one or more of an EPOsp and/or CNPsp fragment into the circulation, the method comprising:
  (a) measuring the level of one or more of an EPOsp and/or CNPsp fragment in a biological sample from the subject; and
  (b) comparing the level of one or more of an EPOsp and/or CNPsp fragment with the level of one or more an EPOsp and/or CNPsp fragment from a control,
  wherein a deviation in the measured level from the control level is indicative of a biological event.

The biological event or disorder includes one or more of acute and chronic renal disease or injury, heart failure, hypertension, syncope, and chronic cardiovascular disease, vascular disease including atherosclerosis, vulnerable plaque, or an acute cardiac syndrome or disorder including myocardial infarctions and angina (unstable), and stable angina.

The applicants have also surprisingly found that in patients with acute myocardial infarction (AMI) the circulating concentration of an EPOsp and/or CNPsp fragment is highest in the first few hours following the onset of the patient's symptoms. Levels observed in the first two to six hours, or four hours were surprisingly very high often reaching a peak some 1.5 to five, commonly two to three fold higher than levels in a normal control population.

In sum, one or more of an EPOsp and/or CNPsp fragment is/are useful as clear early stage markers of, for example, acute coronary syndromes (ACS) such as AMI, particularly non-ST elevated MI, and acute cardiac ischemia, and other disorders as noted herein.

Based on these surprising findings, the applicants have determined for the first time, that it would be useful to screen for one or more of an EPOsp and/or CNPsp or variants or fragments thereof in a biological sample taken from a subject, particularly, for example, within twelve, ten, eight, six, four, two or one hours of onset of, or at clinical presentation with the disorder.

Useful in the invention are antigenic fragments or variants of one or more of an EPOsp and/or CNPsp, which are least 4 or 5 amino acids in length. Particularly useful fragments are at the N-terminus (1-9) or C-terminus of the signal peptides herein. Examples of specific antigenic peptides are shown in SEQ ID NOS:1-6. Both the nucleic acid molecules and peptides form aspects of the invention.

Specific polypeptides of the invention include a polypeptide having the amino acid sequence of any of SEQ ID NOS:1-6 as set forth herein. Also contemplated are variants and fragments of these polypeptides as defined herein, or amino acid sequences having at least about 70%, 75%, 80%, 85%, 90%, 95% or 99% amino acid identity to them. In one embodiment the variants or fragments are functionally equivalent variants or fragments. That is the variants or fragments maintain the function as antigens or signal peptides. Any of the peptides in SEQ ID NOS:1-6 may be used in the preparation of binding agents, for example, antibodies.

Polypeptides, including variant polypeptides and fragments, may be prepared using peptide synthesis methods well known in the art such as direct peptide synthesis using solid phase or automated synthesis. Mutated forms of the polypeptides may also be produced using synthetic methods such as site-specific mutagensis of the DNA encoding the amino acid sequence.

The polypeptides and variant polypeptides and fragments thereof are in one embodiment isolated. They may be isolated or purified from natural sources, or following synthesis, using a variety of techniques that are well known in the art. Technologies include HPLC, ion-exchange chromatography, and immunochromatography but are not limited thereto.

In another aspect, the present invention provides a method for predicting, diagnosing or monitoring an acute cardiac syndrome in a subject, the method comprising: measuring the level of one or more of an EPOsp and/or CNPsp or fragment in a biological sample from the subject and comparing the level of said EPOsp and/or CNPsp or fragments with the level from a control wherein a measured level of is higher than the control level and indicative of ACS.

In another aspect the invention provides a method for monitoring a response to treatment of an ACS or chonic renal disease in a subject, the method comprising measuring the level of one or more of an EPOsp and/or CNPsp or fragment in a biological sample from the subject and comparing the level of said one or more of an EPOsp and/or CNPsp or fragment with the level from a control, wherein a change in the measured level from the control level is indicative of a response to the treatment.

The skilled reader will appreciate that for evaluation purposes, the one or more of an EPOsp and/or CNPsp or fragment level may usefully be compared or correlated with a reference value or control value.

As used herein a control can be an individual or group from which samples of one or more of an EPOsp and/or CNPsp or fragment are taken and a mean level determined Usually, the individual or group will comprise normal healthy individuals or a group of individuals not known to be suffering from a biological event to be monitored. Levels of EPOsp fragments in normal individuals range from between about 14-90 pmol/L (mean is about 50 pmol/L). Levels of CNPsp fragments in normal individuals range from between about 8-50 pmol/L, and the mean control level is about 21 pmol/L. Alternatively, the control level may be assessed based on a plurality of readings from previously tested individuals or groups.

It will be appreciated that the step of measuring levels of one or more of an EPOsp and/or CNPsp or fragment thereof in a sample may be a single measurement on a single sample, or repeated measurements on a number of samples depending on the biological event being studied. In the case of ACS, measurement may comprise, for example, 1 to 20 or more measurements of an EPOsp and/or CNPsp or fragment, 1 to 10, 1 to 5, 1 to 3, or 2 or 3 measurements of one or more of an EPOsp and/or CNPsp or fragment a fragment thereof in samples taken at different times. In one embodiment the measurements are on samples taken within the first twelve, ten, eight, six, five, four, two hours, or within one hour or less of, onset of or clinical presentation with a disorder or suspected disorder. Single, or repeated measurements outside the sample period above may also be taken to establish whether the level of one or more of an EPOsp and/or CNPsp or fragment thereof has fallen to the normal control level, or, for example, cardiac tissue control level.

In one embodiment, the method comprises measuring levels of one or more of an EPOsp and/or CNPsp or fragment thereof in 1 or 2 samples taken within the first hour of onset or presentation, followed by measuring levels of one or more of an EPOsp and/or CNPsp or fragment thereof in 1 or 2 samples taken within two to four hours, or two to three hours of onset or presentation, or initial measurement of the level of one or more of an EPOsp and/or CNPsp or fragment thereof.

As noted above, levels of one or more of an EPOsp and/or CNPsp fragments thereof measured within the first one to twelve, ten, eight, six, four or two hours or less of onset or presentation of an ACS, heart failure, or renal failure, for example, are 1.5 to 10, 1.5 to 5 times higher are usually two to three times higher than levels measured in a normal control.

In one embodiment the prognostic, diagnostic or monitoring tool is calibrated to measure levels of one or more of the peptides or peptide fragments corresponding to any of SEQ ID NOS:1, 2, 3, 4, 5 or 6 (or non-human analogs or variants thereof), or other signal peptide fragments, in the range of, for example, from 0.1 to 1500 pmol/L, 0.1 to 500 pmol/L, 1 to 300 pmol/L, 10 to 250 or 20 to 150 pmol/L. Furthermore, erythropoietin signal peptides may be found in biological samples, including plasma samples, at levels ranging from about 400 to 4000 pmol/L, about 400 to 200 pmol/L, about 320 to 520 pmol/L, or about 400-420 pmol/L or less. Levels at least as low as 5 pmol/L are detectable. Angiotensin signal peptides may be found in biological samples, including plasma samples, at levels ranging from about 10 to 1000 pmol/L, about 5 to 500 pmol/L, about 1 to 100 pmol/L, or about 0.1 to 10 pmol/L or less. Levels at least as low as 0.1 pmol/L are detectable. C-type natriuretic signal peptides may be found in biological samples, including plasma samples, at levels ranging from about 50 to 1500 pmol/L, about 25 to 750 pmol/L, about 10 to 500 pmol/L, or about 5 to 150 pmol/L or less. Levels at least as low as 2 pmol/L are detectable. Endothelin-1 signal peptides may be found in biological samples, including plasma samples, at levels ranging from about 10 to 200 pmol/L, about 5 to 100 pmol/L, about 10 to 50 pmol/L, or about 1 to 20 pmol/L or less. Levels at least as low as 1 pmol/L are detectable.

In another embodiment, a level of one or more of an EPOsp and/or CNPsp or fragment thereof in the sample in the range of about 40 to about 250 pmol/L, about 65 to 250 pmol/L, about 65 to 200 pmol/L, about 70 to 150, or about 70 to 130 pmol/L, is indicative of an ACS.

The biological sample as defined above can be any biological material in which of one or more of an EPOsp and/or CNPsp or fragment thereof can be located or secreted. In one embodiment a biological sample is a circulatory biological sample, for example blood, serum or plasma. In one embodiment, the biological sample is cardiac tissue.

Nucleic Acid Assays

The presence of one or more of an EPOsp and/or CNPspEPOsp and/or CNPsp, or a fragment thereof and the level of expression in a sample may be determined according to methods known in the art such as Southern Blotting, Northern Blotting, FISH or quantative PCR to quantitate the transcription of mRNA,[12] dot blotting, (DNA analysis) or in situ hybridization using an appropriately labelled probe, based on the sequences provided herein. In one embodiment the hybridisation probe is a labelled probe. Examples of labels include fluorescent, chemiluminescent, radioenzyme and biotin-avidin labels. Labelling and visualisation of labelled probes is carried out according to known art methods such as those above. For convenience the nucleic acid probe may be immobilized on a solid support including resins (such as polyacrylamides), carbohydrates (such as sepharose), plastics (such as polycarbonate), and latex beads.

The nucleic acid expression level may be determined using known art techniques such as RT-PCR and electrophoresis techniques including SDS-PAGE. Using these techniques the DNA or cDNA sequence of a nucleic acid molecule of the invention, in a subject sample is amplified, and the level of DNA or cDNA or RNA measured. In an alternate method the DNA, cDNA or RNA level may be measured directly in the sample without amplification. In one embodiment the method is Northern blot hybridization analysis.

Alternatively, the expression level may be measured using reverse transcription based PCR (RT-PCR) assays using primers specific for the nucleic acid sequences. If desired, comparison of the level of one or more of a EPOsp and/or CNPsp polynucleotide in the sample can be made with reference to a control nucleic acid molecule the expression of which is independent of the parameter or condition being measured. A control nucleic acid molecule refers to a molecule in which the level does not differ between the disorder or transplant rejection state and the healthy state. Levels of the control molecule can be used to normalise levels in the compared populations. An example of such a control molecule is GAP-DH. TheEPOsp and/or CNPsp polypeptides and fragments of the invention will change levels with the biological event or disorder.

Peptide Assays

In one embodiment the measuring step comprises detecting binding between one or more of an EPOsp and/or CNPsp, or a fragment thereof and a binding agent that binds, for example, selectively or specifically binds, to one or more of an EPOsp and/or CNPsp or a fragment or variant thereof.

Accordingly, in one embodiment the invention provides an assay for one or more of an EPOsp and/or CNPsp or a fragment or variant thereof in a biological sample, the assay comprising detecting and measuring the level thereof in the sample using any known methods. In one embodiment, the biological sample is obtained from a subject within about twelve, ten, eight, six or four or less hours from onset of an ACS or other disorder related to the concentration or amount of said fragment(s) in a biological sample, or within about twelve, ten, eight, six or four or less of clinical presentation with an ACS, for example, and an EPOsp and/or CNPsp or a fragment thereof are measured.

In one embodiment, the invention provides an assay for one or more of an EPOsp and/or CNPspEPOsp and/or CNPsp, or a fragment thereof comprising:

(a) binding one or more of an EPOsp and/or CNPspEPOsp and/or CNPsp, or a fragment thereof from a biological sample; and (b) measuring the level of bound an EPOsp and/or CNPspEPOsp and/or CNPsp, or a fragment thereof peptides or fragments.

In one embodiment, the target molecule is one or more of SEQ ID NOS:1-6 or a variant or fragment thereof.

In one embodiment, of one or more of an EPOsp and/or CNPsp, or a fragment thereof is bound using a binding agent. The binding agent may be a selective (specific) binding agent. That is, it has low cross-reactivity with other markers of biological events, and more particularly ghrelin. The binding agent in one embodiment is an antibody or a molecule comprising an antigen-binding fragment thereof. Where an antibody is used in the assay, the antibody may be raised against any antigenic part of one or more an EPOsp and/or CNPsp, or a fragment thereof, including within the N-terminus or the C-terminus, so long as it binds a fragment found in a biological sample, preferably a sample in which its presence indicates excretion from a cell. In one embodiment the antibody is raised against a peptide according to any one or more of SEQ ID NOS:1-6 or a variant or fragment thereof.

The present invention also relates to binding agents, including, for example, antibodies, and antigen-binding fragments of the antibodies and their uses. Uses include in an assay, or in the manufacture of an assay, or as a prognostic, diagnostic or monitoring tool are provided as described herein, as are related kits with instructions for use.

Binding agents, for example, antibodies, may be in isolated or purified form. An antibody that binds to one or more of an EPOsp and/or CNPsp, or a fragment or variant thereof may be in any form, including, for example, all classes of polyclonal, monoclonal, single chain, human, humanized antibodies and chimeric antibodies, and other antigen binding constructs. Also included is antiserum obtained by immunizing an animal such as a mouse, rat or rabbit. The antibodies may bind to a common sequence in a group of fragments, or to a specific EPOsp and/or CNPsp fragment, or even to sets of fragments.

A fragment of an antibody or a modified antibody may be used so long as it binds the desired signal peptide or a fragment or variant thereof. The antigen-binding fragment may be, for example, Fab, F(ab'), F(ab'), an Fv fragment or single chain Fv (scFv), in which Fv fragments from H and L chains are ligated by an appropriate linker.[13]

Methods for preparing antibodies, and detecting, modifying and isolating same are well known in the art.[14,15,16] In one embodiment antibodies used are produced by immunizing a suitable host mammal. Fusion proteins comprising one or more of an EPOsp and/or CNPsp, or a fragment thereof may also be used as immunogens.

A binding agent, such as an antibody or other molecule comprising an antigen binding site, may be modified by conjugation with a variety of molecules, such as polyethylene glycol (PEG), biotin, streptavidin, and chemiluminescent, fluorescent, calorimetric, and radioimmunometric labels as discussed herein. The modified antibody can be obtained by chemically modifying an antibody. These modification methods are conventional in the field.

In brief, methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include one or more of an EPOsp and/or CNPsp, or a fragment or variant thereof or a fusion protein thereof. It may be useful to conjugate the immunizing agent to a protein known to be immunogenic in the mammal being immunized. Examples of such immunogenic proteins include but are not limited to keyhole limpet hemocyanin, bovine serum albumin, bovine thyroglobulin, and soybean trypsin inhibitor. Examples of adjuvants which may be employed include Freund's complete adjuvant and MPL TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods well known in the art. The hybridoma cells may be cultured in a suitable culture medium, alternatively, the hybridoma cells may be grown in vivo as ascites in a mammal. Preferred immortalized cell lines are murine myeloma lines, which can be obtained, for example, from the American Type Culture Collection, Virginia, USA Immunoassays may be used to screen for immortalized cell lines which secrete the antibody of interest. One or more of an EPOsp and/or CNPsp, or fragments or variants thereof may be used in screening.

Accordingly also contemplated herein are hybridomas which are immortalized cell lines capable of secreting an EPOsp and/or CNPsp fragment-specific monoclonal antibody.

Well known means for establishing binding specificity of monoclonal antibodies produced by the hybridoma cells include immunoprecipitation, radiolinked immunoassay (RIA), enzyme-linked immunoabsorbent assay (ELISA) and Western blot. For example, the binding affinity of the monoclonal antibody can, for example, be determined by the Scatchard analysis.[14] Samples from immunised animals may similarly be screened for the presence of polyclonal antibodies.

Monoclonal antibodies and other antigen-binding constructs can also be obtained from recombinant host cells. DNA encoding the antibody or antigen-binding construct can be obtained from a hybridoma cell line. The DNA is then placed into an expression vector, transfected into host cells (e.g., COS cells, CHO cells, E. coli cells) and the antibody or antigen-binding construct produced in the host cells. The antibody may then be isolated and/or purified using standard techniques.

To facilitate detection, antibodies and fragments herein may be labelled with detectable markers such as, for example, fluorescent, bioluminescent, and chemiluminescent compounds, as well as radioisotopes, magnetic beads and affinity labels (e.g., biotin and avidin). Examples of labels which permit indirect measurement of binding include enzymes where the substrate may provide for a coloured fluorescent product, suitable enzymes include horseradish peroxidase, alkaline phosphatase, malate dehydrogenase and the like. Fluorochromes (e.g., Texas Red, fluorescein, phycobiliproteins, and phycoerythrin) can be used with a fluorescence activated cell sorter. Labelling techniques are well known in the art.

The monoclonal antibodies, for example, secreted by the cells may be isolated or purified from the culture medium or ascites fluid by conventional immunoglobulin purification procedures such as, for example, reverse phase HPLC, protein A-Sepharose, hydroxyapatite chromatography, gel electrophoresis, dialysis, or affinity chromatography.

Binding of one or more of an EPOsp and/or CNPsp, or a fragment thereof can be detected by any means known in the art including specific (antibody-based) and non-specific (such as HPLC solid phase). Most commonly, antibodies are detected using an assay such as ELISA or RIA as noted above. Competitive binding assays, sandwich assays, non-competitive assays, fluoroimmunoassay, immunofluorometric assay, or immunoradiometric assays, luminescence assays, chemiluniescence assays and mass spectrometry analysis such a surface-enhanced laser desorption and ionization (SELDI) electrospray ionization (ESI), matrix assisted laser-desorption ionization (MALDI), fourier transform Ion cyclotron resonance mass spectroscopy (FTICR) alone or in combination with non-specific binding agents such as chromatography formats are also feasible.

Conveniently, an antibody can be fixed to a solid substrate to facilitate washing and isolation of the polypeptide/antibody complex. Binding of antibodies to a solid support can be achieved using known art techniques. Useful solid substrates for antibodies include glass, nylon, paper and plastics. Similarly, one or more of an EPOsp and/or CNPsp, or a fragment thereof can be adsorbed onto a solid substrate such as adsorbent silica, or resin particles, or silicon chips optionally coated or derivatised with ion exchange, reverse phase (e.g. C18 coating) or other materials. The substrate may be in the form of beads, plates, tubes, sticks or biochips. Examples of biochips include Ciphergen, ProteinChip arrays (Ciphergen Biosystems (CA, USA)), and Packard BioChips available from Perkin Elmer, USA. The biochips may include a chromatographic surface. Biochips or plates with addressable locations and discreet microtitre plates are particularly useful. Also preferred for use are multiplex systems where beads containing antibodies directed to multiple analytes are used to measure levels of the analytes in a single sample. Analytes to be measured may include other markers, e.g., cardiac markers, as well as an EPOsp and/or CNPsp, or variants or fragments thereof. One example of a suitable multiplex bead system for use herein is the Luminex Flurokine Multianalyte Profiling system.

Antibody assay methods are well known in the art see for example U.S. Pat. Nos. 5,221,685, 5,310,687, 5,480,792, 5,525,524, 5,679,526, 5,824,799, 5,851,776, 5,885,527, 5,922,615, 5,939,272, 5,647,124, 5,985,579, 6,019,944, 6,113,855, 6,143,576 and for unlabelled assays U.S. Pat. Nos. 5,955,377 and 5,631,171. All of the documents cited herein are incorporated herein by reference in their entirety.

Immunoassay analysers are also well known and include Beckman Access, Abbott AxSym, Roche ElecSys/Cobas and Dade Behring Status systems amongst others that are well described.

Binding of one or more of an EPOsp and/or CNPsp, or a fragment thereof and an antibody to form a complex can be detected directly or indirectly. Direct detection is carried out using labels such as fluorescence, luminescence, radionuclides, metals, dyes and the like. Indirect detection includes binding detectable labels such as digoxin or enzymes such as horseradish peroxidase and alkaline phosphatase to form a labelled antibody followed by a step of detecting the label by addition of detection reagents.

Horseradish peroxidase for example can be incubated with substrates such as o-Phenylenediamine Dihyhydrochloride (OPD) and peroxide to generate a coloured product whose absorbance can be measured, or with luminol and peroxide to give chemiluminescent light which can be measured in a luminometer as is known in the art. Biotin or digoxin can be reacted with binding agents that bind strongly to them. For example, the proteins avidin and streptavidin will bind strongly to biotin. A further measurable label is then covalently bound or linked thereto either by direct reaction with the protein, or through the use of commonly available crosslinking agents such as MCS and carbodiimide, or by addition of chelating agents.

Generally, the complex is separated from the uncomplexed reagents for example by centrifugation. If the antibody is labelled, the amount of complex will be reflected by the amount of label detected. Alternatively, one or more of an EPOsp and/or CNPsp, or a fragment thereof may be labelled by binding to an antibody and detected in a competitive assay by measuring a reduction in bound labelled polypeptide when the antibody-labelled-polypeptide is incubated with a biological sample containing one or more of an EPOsp and/or CNPsp, or a fragment thereof that is unlabelled. Other immunoassays may be used, for example, a sandwich assay.

In one embodiment, following contact with the antibody, usually overnight for 18 to 25 hours at 4° C., or for 1 to 2 to 4 hours at 25° C. to 40° C., the labelled an EPOsp and/or CNPsp, or a fragment thereof bound to the binding agent (antibody) is separated from the unbound labelled an EPOsp and/or CNPsp, or a fragment thereof. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between an EPOsp and/or CNPsp, or a fragment thereof in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays have greater specificity, speed and greater measuring range. In this type of assay an excess of the primary antibody to an EPOsp and/or CNPsp, or a fragment thereof is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to an EPOsp and/or CNPsp, or a fragment thereof is also incubated with the sample either simultaneously or sequentially with the primary antibody. This second antibody is chosen to bind to a site on an EPOsp and/or CNPsp, or a fragment thereof that is different from the binding site of the primary antibody. These two antibody reactions result in a sandwich with the EPOsp and/or CNPsp, or a fragment thereof from the sample sandwiched between the two antibodies. The second antibody is usually labelled with a readily measurable compound as detailed above for competitive binding assays. Alternatively a labelled third antibody which binds specifically to the second antibody may be contacted with the sample. After washing away the unbound material the bound labelled antibody can be measured and quantified by methods outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

As discussed in the following examples, in one embodiment radioimmunoassay (RIA) is the laboratory technique used. In one RIA a radiolabelled antigen and unlabelled antigen are employed in competitive binding with an antibody. Common radiolabels include $^{125}$I, $^{131}$I, $^{3}$H and $^{14}$C.

Radioimmunoassays involving precipitation of an EPOsp and/or CNPsp, or a fragment thereof with a specific antibody and radiolabelled antibody binding protein can measure the amount of labelled antibody in the precipitate as proportional to the amount of an EPOsp and/or CNPsp, or a fragment thereof in the sample. Alternatively, a labelled an EPOsp and/or CNPsp, or a fragment thereof is produced and an unlabelled antibody binding protein is used. A biological sample to be tested is then added. The decrease in counts from the labelled an EPOsp and/or CNPsp, or a fragment thereof is proportional to the amount of an EPOsp and/or CNPsp, or a fragment thereof in the sample.

In RIA it is also feasible to separate bound EPOsp and/or CNPsp, or a fragment thereof, from free an EPOsp and/or CNPsp, or a fragment thereof. This may involve precipitating the peptide/antibody complex with a second antibody. For example, if the peptide/antibody complex contains rabbit antibody then donkey anti-rabbit antibody can be used to precipitate the complex and the amount of label counted. For example in an LKB, Gammamaster counter.[9]

The methods of the invention further comprise measuring the levels of one or more other markers of kidney disease, cardiovascular disease, etc. The level of the other marker or markers can be compared to mean control levels from a control population. A deviation in the measured level from the mean control level is predictive or diagnostic of or a predisposition to acute or chronic kidney disease, acute or chronic cardiovascular disease, etc.

The methods of the invention have been described with respect to a higher level or increase in levels of an EPOsp and/or CNPsp, or fragment thereof, being indicative of acute coronary syndromes (e.g., AMI and angina), heart failure, vascular disease including atherosclerosis, and chronic renal disease. Measuring deviations above or below a control level are also contemplated.

Other markers include troponin T, troponin I, creatin kinase MB, myoglobin, BNP, NT-BNP, BNP-SP, ANP, ANP-SP, LDH, aspartate aminotransferase, H-FABP, endothelin, adrenomedullin, rennin and angiotensin II. These markers are all implicated in cardiac dysfunction or disease. Kits and reagents for performing such assays are commercially available from a number of suppliers. Correlating the level of an EPOsp and/or CNPsp, or fragment thereof with other markers can increase the predictive, diagnostic or monitoring value of an EPOsp and/or CNPsp, or fragment thereof. In the case of ACS, combining EPOsp and/or CNPsp, or fragment marker levels with known cardiac markers can increase the predictive or diagnostic value of a patient outcome.

Analysis of a number of peptide markers can be carried out simultaneously or separately using a single test sample. Simultaneous, two or multi-site format assays are preferred. Multiplex bead, microassay or biochip systems are particularly useful. The beads, assays or chips can have a number of discreet, often addressable locations, comprising an antibody to one or more markers including an EPOsp and/or CNPsp, or fragment thereof. The one or more markers include more than one an EPOsp and/or CNPsp, or fragment thereof marker. For example, it may be useful to assay for N-terminal and C-terminal an EPOsp and/or CNPsp, or fragment thereof fragments and combine the assay results. Many other such marker combinations are feasible. US2005/0064511 and U.S. Pat. No. 6,019,944 provide a description of microarray, chips, capillary devices and techniques useful in the present invention. Luminex provides a multiplex bead system useful in the present invention. Laboratory analysers suitable for use with separate or sequential assays include AxSym (Abbott, USA), ElecSys (Roche), Access (Beckman), ADVIA CENTAUR® (Bayer) and Nichols Advantage® (Nichols Institute) immunoassay system.

In one embodiment simultaneous assays of a plurality of polypeptides are performed on a single surface such as a chip or array.

In another embodiment separate assays of one or more non-EPOsp and/or CNPsp, or fragment markers are performed and the results collated or combined with EPOsp and/or CNPsp, or fragment marker results.

Where a subject is to be monitored, a number of biological samples may be taken over time. Serial sampling allows changes in marker levels to be measured over time. Sampling can provide information on the approximate onset time of an event, the severity of the event, indicate which therapeutic regimes may be appropriate, response to therapeutic regimes employed, or long-term prognosis. Analysis may be carried out at points of care such as in ambulances, doctors' offices, on clinical presentation, during hospital stays, in outpatients, or during routine health screening, etc.

The methods of the invention may also be performed in conjunction with an analysis of one or more risk factors such as but not limited to age, weight, level of physical activity, sex and family history of events such as obesity, diabetes and cardiac events. Test results can also be used in conjunction with the methods of the invention. For example, glucose tolerance tests, ECG results and clinical examination. A statistically significant change in circulating level of an EPOsp and/or CNPsp, or fragment thereof, together with one or more additional risk factors or test results may be used to more accurately diagnose, prognose or monitor the subject's condition.

Acute Cardiac Syndromes

Applicants have shown that concentrations of various signal peptide fragments are correlated with acute cardiac disorders (FIG. 6). Moreover, levels of an EPOsp and/or CNPsp, or fragment(s) thereof, are at their highest upon clinical presentation in the case of patients presenting with suspected acute myocardial infarction (AMI) or heart attack. Patients presenting with acute cardiac syndromes or disorders, and in particular acute cardiac ischemia coronary artery disease caused by (heart attack leaving scarring in the heart muscle or myocardium) may or may not experience subsequent myocardial infarction (MI). The group which does not experience MI cannot be readily diagnosed using current clinical techniques and markers. Applicants have provided a useful early and specific marker for myocardial damage associated with MI, for example. This will allow the early diagnosis of myocardial damage due to adverse events and allow a physician to distinguish such cases from other acute coronary syndromes, including angina, as well as from other causes of chest pain (e.g., gastro-intestinal disease, lung/pleural disorders and the like). This significantly shortens the window currently experienced waiting for elevation of levels of current cardiac biomarkers such as myoglobin, CK-MB, TnT and TnI. A more precise diagnosis and treatment can also be effected earlier, reducing morbidity and mortality and providing better prognostic outcomes.

In another embodiment, the invention has application in monitoring reperfusion treatment in cardiac patients. Reperfusion treatment commonly includes percutaneous coronary intervention (eg angioplasty) and/or pharmacological treatment. Thrombolytic drugs for revascularisation are commonly employed in pharmacological treatment. Adjunctive therapies include anticoagulant and anti-platelet therapies. Reperfusion treatment is most effective when employed as soon as possible after diagnosis. Use of analysis of EPOsp and/or CNPsp, or fragment(s) thereof, to accelerate diagnosis allows prompt introduction of reperfusion treatment. Effectiveness of treatment can also be monitored by repeat testing, and therapy adjusted as appropriate. For a comprehensive discussion of reperfusion treatment see Braunwald et al. herein.[3]

Cardiac Disease

The methods of the invention may also be useful to diagnose or predict cardiac disease in a subject by analysis of an EPOsp and/or CNPsp, or fragment(s) thereof, particularly in biological samples taken from the circulation (or biological samples derived from such samples).

Blood Doping

Applied to the spectrum of agents that athletes can choose from to illegally boost performance, proteins and peptides provide an attractive option. In one aspect, the invention provides a solution to this problem. When produced by synthetic or recombinant technologies, proteins such as EPO are made to mimic as closely as possible the endogenous counterpart present in the circulation or tissue. This entails removal either a priori or a posteriori of components that would render the molecule vulnerable to easy detection. One such component is a region of the molecule known as the signal peptide. It was thought that signal peptide sequences derived from the endogenous production of proteins underwent intracellular destruction and were therefore absent from the circulation. However, we have developed novel immunoassay technologies to demonstrate that signal peptide sequences of EPO is not only present in the circulation of humans, but may also be measured in urine (or another bodily fluid, tissue sample, etc.). The EPO signal peptide sequence is very short in comparison with full length natural or recombinant EPO and has a much simpler primary and tertiary structure, without glycosylations, rendering it much easier to measure by existing assay formats. An immunoassay directed towards the signal peptide of human EPO is described herein, which is sensitive for immunoreactive human EPO signal peptide (EPOsp) and can detect circulating levels down to <20 fmol/ml (<640 pg/ml). Utilizing this assay, we have determined in normal human plasma, a ratio of EPOsp:EPO as approximately 6:1. However, in patients with chronic renal failure this ratio rises to approximately 10:1, whereas in patients with heart failure the ratio is approximately 3:1. Thus, there is a differential response of EPOsp:EPO ratio in patients with different disease states. Applying this paradigm to athletes doping with or otherwise misusing recombinant EPO, the plasma EPOsp:EPO ratio could be expected to be less than 1:1, including 1:10, 1:100, 1:1000, or less during, for example, the acute phase of administration. After repeated administration of rEPO, circulating levels of EPOsp will be much lower than normal drug-free levels, due to changes in endogenous secretion and excretion. Furthermore, as EPOsp is a much smaller molecule than EPO itself, its renal clearance and subsequent urinary presence will display a marked variation with prominent swings in ratio when compared with plasma EPOsp.

Kits

Most usually, kits will be formatted for assays known in the art, and in certain embodiments for RIA or ELISA assays, as are known in the art.

The kits may also include one or more additional markers for the disorders noted herein. In the case of ACS, for example, the additional marker may include one or more of troponin T, troponin I, creatin kinase MB, myoglobin, ANP, BNP, BNP-SP, ANP, ANP-SP, NT-BNP, LDH, aspartate aminotransferase, H-FABP, endothelin, adrenomedullin, rennin and angiotensin II. In one embodiment all of a subset of the markers are included in the kit.

The kit may be comprised of one or more containers and may also include collection equipment, for example, bottles, bags (such as intravenous fluids bags), vials, syringes, and test tubes. At least one container will be included and will hold a product which is effective for predicting, diagnosing, or monitoring a biological event such as acute or chronic kidney disease, acute or chronic cardiovascular disease, ACS, etc. The product is usually a polypeptide and/or a binding agent, particularly an antibody or antigen-binding fragment of the invention, or a composition comprising any of these. In a preferred embodiment, an instruction or label on or associated with the container indicates that the composition is used for predicting, diagnosing, or monitoring the biological event. Other components may include needles, diluents and buffers. Usefully, the kit may include at least one container comprising a pharmaceutically-acceptable buffer, such as phosphate-buffered saline, Ringer's solution or dextrose solution.

Binding agents that selectively bind EPOsp and/or CNPsp, or fragment(s) thereof are desirably included in the kit. In one embodiment, the binding agent is an antibody, preferably an antibody or antigen-binding fragment of the invention. The antibody used in the assays and kits may be monoclonal or polyclonal, for example, and may be prepared in any mammal as discussed above, and includes antibody fragments and antibodies prepared using native and fusion peptides, for example.

In one kit embodiment a target peptide detection reagent is immobilized on a solid matrix, for example, a porous strip or chip to form at least one detection site for an EPOsp and/or CNPsp, or a fragment(s) thereof. The measurement or detection region of the porous strip may include a plurality of detection sites, such detection sites containing a detection reagent. The sites may be arranged in a bar, cross or dot or other arrangement. A test strip or chip may also contain sites for negative and/or positive controls. The control sites may alternatively be on a different strip or chip. The different detection sites may contain different amounts of immobilized nucleic acids or antibodies, e.g., a higher amount in the first detection site and lower amounts in subsequent sites. Upon the addition of a test biological sample the number of sites displaying a detectable signal provides a quantitative indication of the amount of an EPOsp and/or CNPsp, or a fragment(s) thereof present in the sample.

Also included in the kit may be a device for sample analysis comprising a disposable testing cartridge with appropriate components (markers, antibodies and reagents) to carry out sample testing. The device will conveniently include a testing zone and test result window. Immunochromatographic cartridges are examples of such devices. See for example U.S. Pat. Nos. 6,399,398; 6,235,241 and 5,504,013.

Alternatively, the device may be an electronic device which allows input, storage and evaluation of levels of the measured marker against control levels and other marker levels. US 2006/0234315 provides examples of such devices. Also useful in the invention are Ciphergen's Protein Chip® which can be used to process SELDI results using Ciphergen's Protein Chip® software package.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

EXAMPLE 1

Methods

All human protocols were approved by the Upper South Regional Ethics Committee of the Ministry of Health, New Zealand and were performed in accord with the Declaration of Helsinki.

Chemicals

Synthetic human signal peptide fragments corresponding to EPOsp and CNPsp were synthesised using a mild Fmoc Solid Phase Synthesis method.[4,9] All buffer reagents were purchased from BDH® (UK) and/or Sigma (Mo, USA). EPOsp(1-9) and CNPsp(14-23) were all synthesised with an extended cysteine (C- or N-terminus) for directional carrier coupling. EPOsp(1-9) and CNPsp(14-23), tyrosyl-containing peptides were also synthesised for tracer preparation.

Human Studies

Non-fasting blood samples were collected from the following groups of patients presenting at Christchurch Hospital, New Zealand:

1) 55 normal, healthy volunteers. Samples were collected into EDTA blood tubes, centrifuged and the plasma stored at −80° C. until analysis.
2) 10 patients with acutely decompensated heart failure (CHF). Samples were taken at presentation, 24-48 hours (CHF). Samples were taken at presentation, 24-48 hours after admission and at hospital discharge.
3) 23 ST-elevation myocardial infarction (STEMI) patients. Samples were drawn on admission to the Coronary Care Unit (time 0) and thereafter at 00.5, 1, 2, 4, 8, 12, 24 and 72 hours as in patients, samples were taken into tubes on ice and centrifuged at +4° C. at 2700 g for 5 min and the plasma stored at −80° C. until analysed.
4) 75 patients with end stage renal disease. Samples were drawn into EDTA collection tubes at a hospital outpatient visit, centrifuged to prepare plasma and stored at −80° C.

Plasma Extraction

All plasma samples were extracted on SepPak Cartridges, (Waters, USA) as previously described,[9] dried and stored at −20° C. prior to RIA and HPLC.

Hormone Concentration Analysis

Plasma samples were assayed for Tn1, CK-MB, Myoglobin and Insulin using heterologous immunoassays on an Elecsys 2010 (Roche, USA) using ruthenium labelled biotinylated antibodies according to standard manufacturers protocols.

EPOsp and CNPsp fragments were measured by specific RIA as follows:

EPOsp(1-9) and CNPsp(14-23) RIA

For the measurement of circulating human EPOsp(1-9) and CNPsp(14-23) peptides, we generated a novel and specific immunoassays.

Antibody Generation

Each antigenic residue sequence, containing either a N- or C-terminally linked cysteine, was coupled to malemide treated N-e-maleimidocaproyloxy succinimide ester (EMCS) derivatised BSA in PBS (pH 7.0) by gentle mixing at room temperature. Coupled peptide was emulsified with Freund's (2 ml) adjuvant and injected subcutaneously (2 ml total) in 2 sheep over 4-5 sites at monthly intervals. Sheep were bled 12 days after injection to assess antibody titres until adequate levels were achieved. For immunoassay, EPOsp and CNPsp immunoreactivity were determined using antiserum within the final dilution range of 1:6,000-1:45,000. Each antiserum had no detectable cross reactivity with peptides and drugs indicated in FIG. 6. including human proBNP (1-13), proBNP (1-76), proANP (1-30), insulin, angiotensin II, angiotensin (1-7), urotensin II, CNP, ghrelin, C-ghrelin (52-117), proCNP (1-15), adrenomedulin, urocortin I, urocortin II, BNP-SPn(1-10), ANP-SPc (16-25), ANP-SP (1-10), INS-SPn (1-9). Cross reactivity was assessed following standardised protocols well known in the art.[10]

Iodination and Assay Method

Each antigenic residue, containing either a N- or C-terminal tyrosine residue, was iodinated via the Chloramine T method and purified on reverse phase HPLC (RP-HPLC). From this preparation an iodinated tracer form after RP-HPLC was tested. All samples, standards, radioactive traces and antiserum solutions were diluted in potassium based assay buffer.[4,9] Each assay incubate consisted of 100 µL sample or standard (the appropriate synthetic antigenic peptide sequence) and 100 µL specific antigen-antiserum which was vortexed and incubated at 4° C. for 24 hours. 100 µL of trace (4000-5000 cpm) was then added and further incubated for 24 hours at 4° C. Free and bound immunoreactivities were finally separated by solid phase second antibody method (donkey anti-sheep Sac-Cel®, IDS Ltd, England) and counted in a Gammamaster counter (LKB, Uppsala, Sweden Statistical Analysis All results are presented as mean±SEM. Time-course data were analysed using two-way ANOVA for repeated measurements followed by least significant difference post-hoc testing. Correlation analysis of plasma hormone concentrations was carried out using a general linear regression model. In all analyses, a P-value <0.05 was considered significant.

Results

Respective venous plasma concentrations (in pmol/L) measured for EPOsp and CNPsp fragments in healthy humans are below:

| | |
|---|---|
| EPOsp fragment | 49.9 ± 3.7 |
| CNPsp fragment | 20.7 ± 3.1 |

In healthy humans, concentrations of EPOsp and CNPsp in blood do not show a significant correlation with BMI. Having established that EPOsp and CNPsp fragments are present in human plasma we then measured serial concentrations of immunoreactive EPOsp and CNPsp in patients with documented AMI. Highest concentrations of immunoreactive EPOsp and/CNPsp were observed hours after hospital admission and slowly dropped to stable levels over about eight hours Importantly, average peak EPOsp and CNPsp fragment levels were 2 to 3 fold higher (range two to 5 fold higher) than levels in normal healthy volunteers. Peak concentrations of myoglobin occurred 1-2 hours after hospital admission, whereas peak TnI and CK-MB levels were not attained until 8-12 hours after admission.

EXAMPLE 2

Figure 2:
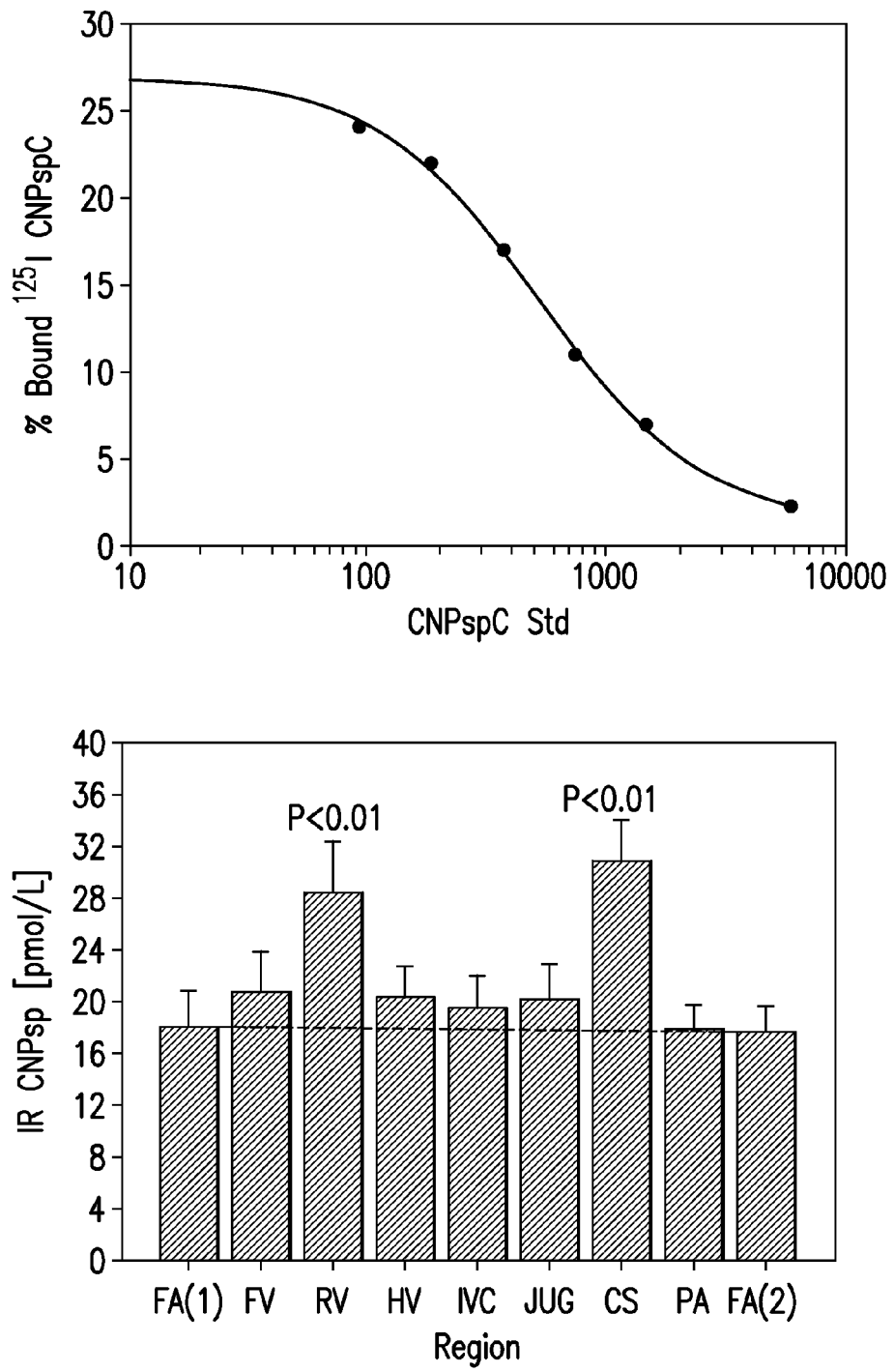
FIG. 2 (upper panel) a representative standard curve of a CNPsp(15-23) RIA. (Lower panel): sampling of regional vascular beds in humans shows that only the cardiac coronary sinus (CS) and renal vein (RV) had higher CNPsp concentrations compared with circulating arterial (FA1 and FA2) levels. This indicates that heart is a functional source of CNPsp and that one may sample a desired venous source with no need to sample an arterial source. The signal peptide may be identified in an arterial sample, but a venous sample may be used to identify the source of the peptide.
Figure 3:
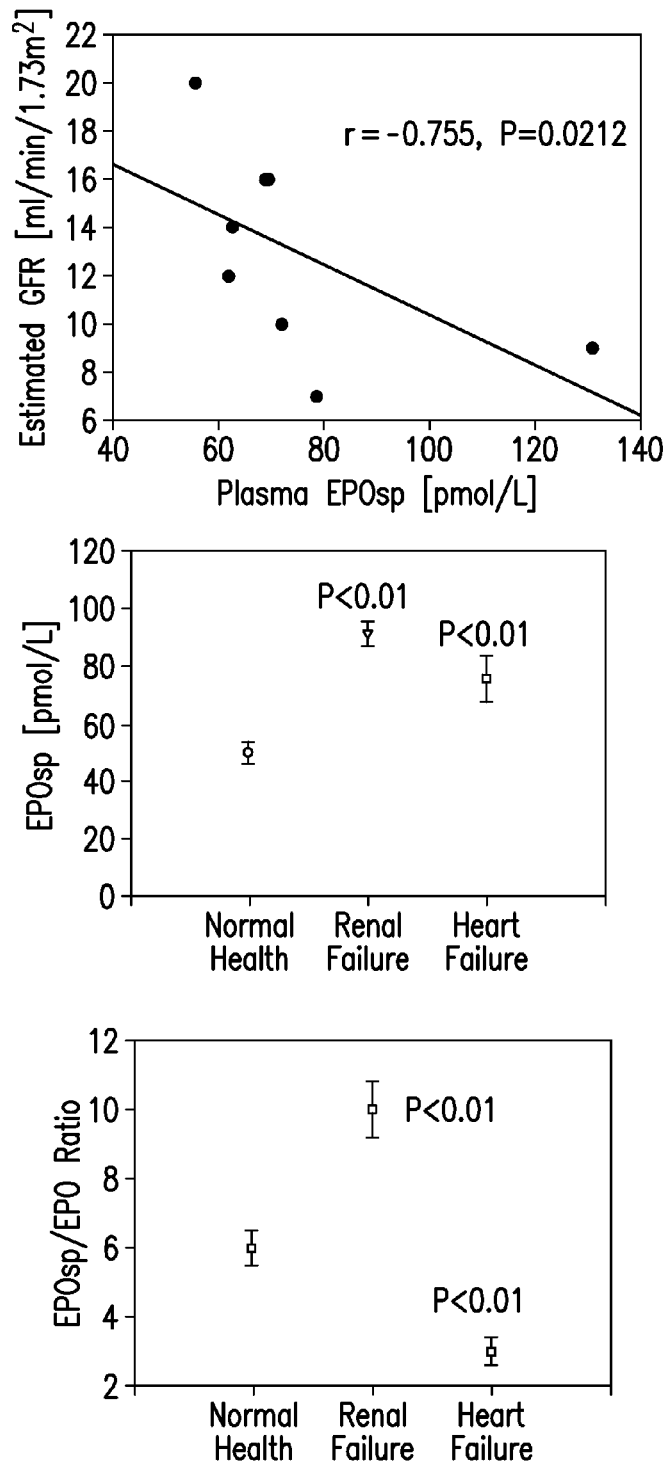
FIG. 3 (upper panel) plasma EPOsp(1-9) levels show a negative correlation with GFR (an indicator of renal function). (Middle panel) plasma EPOsp levels are elevated in patients with chronic renal disease (while EPO drops markedly) and in those with heart failure where EPOsp levels are elevated (while EPO rises markedly) compared with normal. (Lower panel) the ratio of EPOsp (pmol/L) to EPO (mU/L) is about 6 in normal health. This rises to approximately 10 in renal disease and drops to about 4 in heart failure patients.
Figure 4:
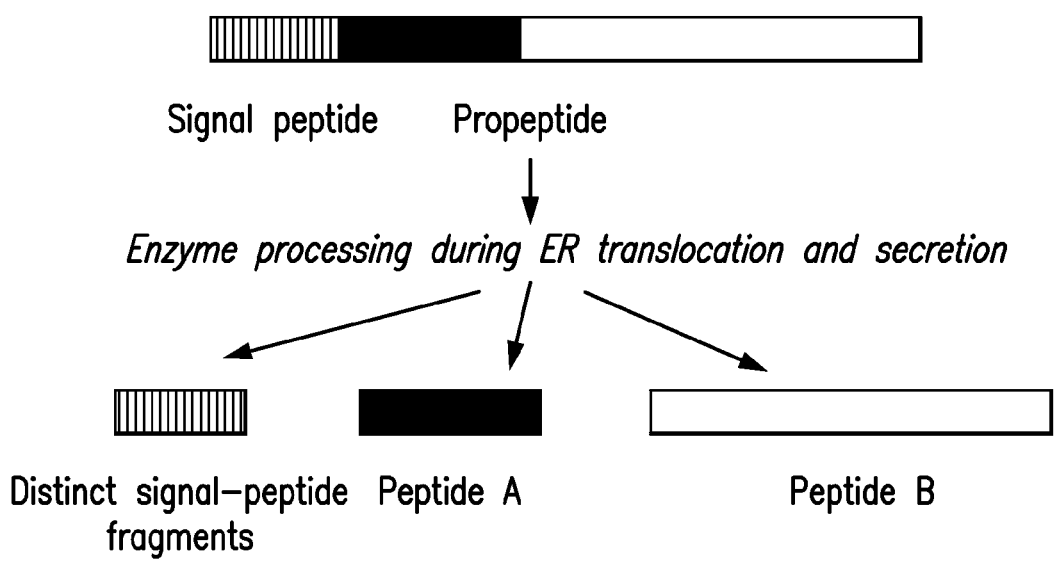
FIG. 4 shows a generalised schematic of signal peptide cleavage from prepropeptide precursor molecules and indicates the generation of previously unknown and unrecognized, detectable signal peptide fragments.

Eight patients with clinically stable suspected ACS were catheterized and blood samples from multiple organ sites: these were the femoral artery FA(1) and FA(2) femoral vein (FV), renal vein (RV), hepatic vein (HV), inferior vena cava (IVC), jugular (JUG), cardiac coronary sinus vein (CS) and pulmonary artery (PA). Blood was collected into chilled EDTA tubes, prepared from plasma by centrifugation and the plasma submitted to immunoreactive EPOsp and CNPsp RIAs. FIG. 2 clearly shows that the highest site of immunoreactive CNPsp concentration is the CS, the vein draining the heart, especially the ventricles. This is evidence that the heart can secrete immunoreactive CNPsp (e.g., CNPsp fragments) Immunoreactive EPOsp, particularly in the form of EPOsp fragments, can also be secreted.

EXAMPLE 3

Plasma extracts from 10 patients with acute decompensated heart failure and 75 patients with chronic renal failure were subjected to specific EPOsp and EPO immunoassay. Top panel: estimated glomerular filtration rate (eGFR) in 10 patients with chronic renal failure. There was a statistically significant negative relationship between eGFR and plasma EPOsp. Middle panel: Plasma EPOsp concentrations in normal healthy individuals, patients with chronic renal failure and in patients with decompensated acute heart failure. Plasma concentrations of EPOsp are significantly elevated in patients with chronic renal failure and heart failure. Lower panel: the ratio of EPOsp/EPO in normal heaoth, chronic renal failure and acute heart failure. The ratio in normal health is approximately 6:1, whereas in chronic renal failure the ratio increases significantly (compared with normals) to approximately 10:1. In contrast, in acute heart failure, the ratio of EPOsp to EPO is significantly reduced (compared with normals) to approximately 3:1.

CONCLUSION

Circulating EPOsp and CNPsp concentrations in clinically stable patients are likely derived from cardiac sources. The significant cardiac secretion is consistent with EPOsp and CNPsp being cardiac hormones.

DISCUSSION

This evidence is the first to document EPOsp and CNPsp fragments as being present in the circulation and extracellular space within two hours of a patient presenting with ACS or within two hours of the onset of ACS. We show in the first instance that the measurement of immunoreactive EPOsp and CNPsp in blood has potential as a rapid biomarker of acute cardiac ischemia and/or subsequent injury and in the second instance, that measurement of immunoreactive EPOsp and CNPsp after the event has potential merit as a marker of long term prognosis and outcome.

We also show that measurement of immunoreactive EPOsp and CNPsp has potential use in acute or chronic kidney disease and the potential to act as biomarkers of acute or chronic kidney function/dysfunction.

Those skilled in the art will of course appreciate that the above description is provided by way of example and that the invention is not limited thereto.

CITED DOCUMENTS

1. Universal definition of myocardial infarction. Consensus statement from the Joint ESC/ACCF/AHA/WHF Taskforce for the redefinition of myocardial infarction. Circulation 2007 116:2634-2653.
2. National Academy of Clinical Biochemistry and IFCC Committee for standardisation of markers of cardiac damage laboratory medicine practice guidelines: analytical issues for biochemical markers of acute coronary syndromes. Circulation 2007 115:e352-e355.
3. Braunwald E, Zipes D P, Libby P. Acute myocardial infarction Chp. 35 Heart disease: a textbook of cardiovascular medicine, $6^{th}$ ed. 2001. pgs. 1114-1231.
4. Richards A M, Nicholls M G, Yandle T G, Frampton C, Espiner E A, Turner J G, Buttimore R C, Lainchbury J G, Elliott J M, Ikram H, Crozier I G, Smyth D W. Plasma N-terminal pro-brain natriuretic peptide and adrenomedullin: new neurohormonal predictors of left ventricular function and prognosis after myocardial infarction. Circulation 1998 97:1921-1929.
5. Jernberg T, Stridsberg M, Venge P, Lindahl B. N-terminal pro Brain Natriuretic Peptide on admission for early risk stratification of patients with chest pain and no ST-segment elevation. J. Am. Coll. Cardiology 2002 40:437-445.
6. Omland T, Persson A, Ng L, O'Brien R, Karlsson T, Herlitz J, Hartford M, Caidahl K. N-terminal pro-B-type natriuretic peptide and long-term mortality in acute coronary syndromes. Circulation. 2002 106: 2913-2918.
7. Naghavi M, Libby P, Falk E, Casscells S W, Litovsky S, Rumberger J, Badimon J J, Stefanadis C, Moreno P, Pasterkamp G, Fayad Z, Stone P H, Waxman S, Raggi P, Madjid M, Zarrabi A, Burke A, Yuan C, Fitzgerald P J, Siscovick D S, de Korte C L, Aikawa M, Airaksinen K E, Assmann G, Becker C R, Chesebro J H, Farb A, Galis Z S, Jackson C, Jang I K, Koenig W, Lodder R A, March K, Demirovic J, Navab M, Priori S G, Rekhter M D, Bahr R, Grundy S M, Mehran R, Colombo A, Boerwinkle E, Ballantyne C, Insult W Jr, Schwartz R S, Vogel R, Serruys P W, Hansson G K, Faxon D P, Kaul S, Drexler H, Greenland P, Muller J E, Virmani R, Ridker P M, Zipes D P, Shah P K, Willerson J T. From vulnerable plaque to vulnerable patient: a call for new definitions and risk assessment strategies: Part II Circulation 2003 108: 1772-1778.
8. Ronco C, Haapio M, House A A, Anavekar N, Bellomo R. Cardiorenal syndrome. J. Am. Coll. Cardiol. 2008 52:1527-1539.
9. Hunt P J, Richards A M, Nicholls M G, Yandle T G, Doughty R N, Espiner E A. Immunoreactive amino terminal pro brain natriuretic peptide (NT-proBNP): a new marker of cardiac impairment. Clin. Endocrinol. 1997 47:287-296.
10. The Immunoassay Handbook. 3$^{rd}$ edition, ed. David Wild. Elsevier Ltd, 2005.
11. Braud V M, Allan D S, O'Callaghan C A, Soderstrom K, D'Andrea A, Ogg G S, Lazetic S, Young N T, Bell J I, Phillips J H, Lanier L L, McMichael A J. HLA-E binds to natural killer cell receptors CD94/NKG2A, B and C. Nature 1998 391:795-799.
12. Thomas P S. Hybridization of denatured RNA and small DNA fragments transferred to nitrocellulose Proc. Natl. Acad. Sci. USA 1980 77:5201-5205.
13. Huston J S, D Levinson, M Mudgett-Hunter, M S Tai, J Novotný, M N Margolies, R J Ridge, R E Bruccoleri, E Haber, R Crea. Protein engineering of antibody binding sites: recovery of specific activity in an anti-digoxin single-chain Fv analogue produced in *Escherichia coli* Proc. Natl. Acad. Sci. USA 1988 85:5879-5883.
14. Harbour E, Lane D. Antibodies: A Laboratory Manual. 1988 Cold Spring Harbour Press New York.
15. Kohler G, Milstein C. Continuous Cultures of Fused Cells Secreting Antibody of Predefined Specficity. Nature 1975 256: 495-497.
16. Verhoeyen M, Milstein C, Winter G. Reshaping human antibodies: grafting an antilysozyme activity. Science 1988 239: 1534-1536.

All citations in this list and throughout the specification including patent specifications are hereby incorporated in their entirety.

---

The invention claimed is:

1. An antibody, or antigen-binding fragment thereof, which specifically binds a peptide of C-type natriuretic signal peptide CNPsp selected from CNPsp(1-13) peptide having an amino acid sequence consisting of SEQ ID NO:5 or CNPsp(14-23) peptide having an amino acid sequence consisting of SEQ ID No:6,
   wherein the antibody, or antigen-binding fragment thereof is immobilized on a solid matrix or is labeled.

2. The antibody, or antigen-binding fragment thereof, of claim 1, wherein the antibody, or antigen-binding fragment thereof, is a polyclonal, monoclonal, chimeric, or humanized antibody or antigen-binding fragment thereof.

3. The antibody, or antigen-binding fragment thereof, of claim 1 wherein the antibody, or antigen-binding fragment thereof, is labelled with a detectable marker.

4. The antibody, or antigen-binding fragment thereof, of claim 1, wherein the antibody, or antigen-binding fragment thereof, specifically binds CNPsp(1-13) peptide having an amino acid sequence consisting of SEQ ID NO:5.

5. The antibody, or antigen-binding fragment thereof, of claim 1, wherein the antibody, or antigen-binding fragment thereof, specifically binds CNPsp(14-23) peptide having an amino acid sequence consisting of SEQ ID NO:6.

6. The antibody, or antigen-binding fragment thereof, of claim 1, wherein the antibody, or antigen-binding fragment thereof, is in a complex bound to a C-type natriuretic signal peptide (CNPsp) to which the antibody, or antigen-binding fragment thereof, specifically binds.

7. The antibody, or antigen-binding fragment thereof, of claim 1, wherein the antibody, or antigen-binding fragment thereof, is immobilized on a solid matrix.

8. The antibody, or antigen-binding fragment thereof, of claim 6, wherein the antibody, or antigen-binding fragment thereof, is immobilized on a solid matrix.

9. A composition comprising:
   a first anti-C-type natriuretic signal peptide (CNPsp) antibody, or antigen-binding fragment thereof, immobilized on a solid matrix;
   a CNPsp or fragment thereof bound to the first anti-CNPsp antibody, or antigen-binding fragment thereof; and
   a second anti-CNPsp antibody, or antigen-binding fragment thereof, bound to the CNPsp or fragment thereof, wherein the second anti-CNPsp antibody, or antigen-binding fragment thereof, binds to a site on CNPsp or fragment thereof that is different from the site bound by the first anti-CNPsp antibody, or antigen-binding fragment thereof, wherein
   either the first or the second anti-CNPsp antibody, or antigen-binding fragment thereof, is the anti-CNPsp antibody, or antigen-binding fragment thereof, which specifically binds a peptide of CNPsp selected from CNPsp(1-13) peptide having an amino acid sequence consisting of SEQ ID NO:5 or CNPsp(14-23) peptide having an amino acid sequence consisting of SEQ ID NO:6.

10. The composition of claim 9, wherein the second anti-CNPsp antibody, or antigen-binding fragment thereof, is labeled.

11. The composition of claim 9, wherein either the first or the second anti-CNPsp antibody, or antigen-binding fragment thereof, binds the CNPsp(1-13) peptide having an amino acid sequence consisting of SEQ ID NO:5.

12. The composition of claim 9, wherein either the first or the second anti-CNPsp antibody, or antigen-binding fragment thereof, binds the CNPsp(14-12) peptide having an amino acid sequence consisting of SEQ ID NO:6.

13. A kit comprising:
   a first anti-C-type natriuretic signal peptide (CNPsp) antibody, or antigen-binding fragment thereof, immobilized on a solid matrix; and
   a second anti-CNPsp antibody, or antigen-binding fragment thereof, wherein the second anti-CNPsp antibody, or antigen-binding fragment thereof, binds to a site on CNPsp or fragment thereof that is different from the site bound by the first anti-CNPsp antibody, wherein
   either the first or the second anti-CNPsp antibody, or fragment thereof, is the anti-CNPsp antibody, or antigen-binding fragment thereof, which specifically binds a peptide of CNPsp selected from CNPsp(1-13) peptide having an amino acid sequence consisting of SEQ ID NO:5 or CNPsp(14-23) peptide having an amino acid sequence consisting of SEQ ID NO:6.

14. The kit of claim 13, wherein the second anti-CNPsp antibody, or antigen-binding fragment thereof, is labeled.

15. The kit of claim 13, wherein either the first or the second anti-CNPsp antibody, or antigen-binding fragment thereof, binds the CNPsp(1-13) peptide having an amino acid sequence consisting of SEQ ID NO:5.

16. The kit of claim 13, wherein either the first or the second anti-CNPsp antibody, or antigen-binding fragment thereof, binds the CNPsp(14-23) peptide having an amino acid sequence consisting of SEQ ID NO:6.

17. The kit of claim 13, wherein the solid matrix is a porous strip or chip.

* * * * *

UNITED STATES PATENT AND TRADEMARK OFFICE
CERTIFICATE OF CORRECTION

PATENT NO. : 9,994,631 B2  Page 1 of 1
APPLICATION NO. : 14/691562
DATED : June 12, 2018
INVENTOR(S) : Christopher Joseph Pemberton It is certified that error appears in the above-identified patent and that said Letters Patent is hereby corrected as shown below:

In the Claims

Column 36, Line 42, delete "CNPsp(14-12)" and insert --CNPsp(14-23)--

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 27
<212> TYPE: PRT
<213> ORGANISM: Homo sapiens

<400> SEQUENCE: 1

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 2
<211> LENGTH: 9
<212> TYPE: PRT
<213> ORGANISM: Homo sapiens

<400> SEQUENCE: 2

Met Gly Val His Glu Cys Pro Ala Trp
1               5

<210> SEQ ID NO 3
<211> LENGTH: 10
<212> TYPE: PRT
<213> ORGANISM: Homo sapiens

<400> SEQUENCE: 3

Ser Leu Pro Leu Gly Leu Pro Val Leu Gly
1               5                   10

<210> SEQ ID NO 4
<211> LENGTH: 23
<212> TYPE: PRT
<213> ORGANISM: Homo sapiens

<400> SEQUENCE: 4

Met His Leu Ser Gln Leu Leu Ala Cys Ala Leu Leu Leu Thr Leu Leu
1               5                   10                  15

Ser Leu Arg Pro Ser Glu Ala
            20
```

```
<210> SEQ ID NO 5
<211> LENGTH: 13
<212> TYPE: PRT
<213> ORGANISM: Homo sapiens

<400> SEQUENCE: 5

Met His Leu Ser Gln Leu Leu Ala Cys Ala Leu Leu Leu
1               5                   10

<210> SEQ ID NO 6
<211> LENGTH: 10
<212> TYPE: PRT
<213> ORGANISM: Homo sapiens

<400> SEQUENCE: 6

Thr Leu Leu Ser Leu Arg Pro Ser Glu Ala
1               5                   10
```